US012741127B2

(12) United States Patent
Roux et al.

(10) Patent No.: US 12,741,127 B2
(45) Date of Patent: Sep. 22, 2026

(54) TRANSDERMAL PERMEANT APPLICATION DEVICE

(71) Applicant: PassPort Technologies, Inc., La Jolla, CA (US)

(72) Inventors: Serge Roux, Boston, MA (US); Christopher Kadamus, West Roxbury, MA (US); Bernadette C. Messier, Roswell, GA (US); Uros Kascak, La Jolla, CA (US); Nathan Barr, Portland, ME (US)

(73) Assignee: PassPort Technologies, Inc., La Jolla, CA (US)

( * ) Notice: Subject to any disclaimer, the term of this patent is extended or adjusted under 35 U.S.C. 154(b) by 278 days.

(21) Appl. No.: 17/818,222

(22) Filed: Aug. 8, 2022

(65) Prior Publication Data

US 2023/0067488 A1 Mar. 2, 2023

Related U.S. Application Data

(63) Continuation of application No. 16/075,376, filed as application No. PCT/JP2017/004835 on Feb. 3, 2017, now Pat. No. 11,446,478.

(Continued)

(51) Int. Cl.

*A61M 37/00* (2006.01)
*A61N 1/04* (2006.01)

(Continued)

(52) U.S. Cl.

CPC .......... *A61M 37/00* (2013.01); *A61N 1/0492* (2013.01); *A61N 1/303* (2013.01); *A61N 1/327* (2013.01);

(Continued)

(58) Field of Classification Search

CPC .......... A61M 37/00; A61M 2037/0007; A61M 2037/0023; A61N 1/0492; A61N 1/303; A61N 1/327

See application file for complete search history.

(56) References Cited

U.S. PATENT DOCUMENTS 1,949,271 A * 2/1934 Duhamel .......... A61F 13/0203 D24/189
4,176,664 A * 12/1979 Kalish .......... A61F 13/0203 604/290

(Continued)

FOREIGN PATENT DOCUMENTS

EP 0817659 B1 * 5/2001 .......... A61N 1/0444
EP 0729366 B1 7/2002

(Continued)

OTHER PUBLICATIONS

European Search Report in European Application No. 1777624.9 dated Jun. 13, 2019, in 8 pages.

(Continued)

*Primary Examiner* — Bhisma Mehta
*Assistant Examiner* — Mark A Igel
(74) *Attorney, Agent, or Firm* — Knobbe, Martens, Olson & Bear LLP

(57) ABSTRACT

The device of the present invention comprises an intervening release liner as a common special feature, and the intervening release liner covers a part of an adhesive surface of a patch. The intervening release liner gets away from the patch, and is fixed to a patch application support (or porator tab). Due to such constitution, under a situation in use where the first part of the adhesive area of the patch adheres to a skin surface, the patch application support is slidable along (Continued)

the skin surface while peeling the intervening release liner from said part of the adhesive area of the patch to adhere to the skin surface.

19 Claims, 30 Drawing Sheets

Related U.S. Application Data

(60) Provisional application No. 62/291,752, filed on Feb. 5, 2016.

(51) Int. Cl.
*A61N 1/30* (2006.01)
*A61N 1/32* (2006.01)

(52) U.S. Cl.
CPC ............... *A61M 2037/0007* (2013.01); *A61M 2037/0023* (2013.01)

(56) References Cited

U.S. PATENT DOCUMENTS 5,383,900 A * 1/1995 Krantz ................. A61B 17/085 602/903
6,148,232 A * 11/2000 Avrahami ............. A61N 1/327 604/20
D574,500 S * 8/2008 Koch ........................... D24/189
D605,775 S * 12/2009 Koch ........................... D24/189
8,116,860 B2 * 2/2012 Messier ............... A61N 1/0428 604/20
9,918,665 B2 * 3/2018 McRae .................. A61N 1/303
11,446,478 B2 * 9/2022 Roux ..................... A61N 1/303
2004/0181203 A1 * 9/2004 Cormier ............ A61M 37/0015 604/289
2008/0208107 A1 * 8/2008 McRae ................ A61N 1/0412 604/20
2009/0149897 A1 * 6/2009 Dacey, Jr. ......... A61M 5/14276 607/3
2009/0270884 A1 * 10/2009 Hake ..................... A61F 15/002 606/139
2013/0018337 A1 * 1/2013 Kydonieus ........... A61K 31/567 604/307
2013/0211347 A1 * 8/2013 Arbel .................. A61K 9/7084 604/290

FOREIGN PATENT DOCUMENTS

JP S63-125133 A 5/1988
JP 2008104542 A * 5/2008
JP 2012024240 A * 2/2012 ........ A61M 37/0015
JP 2013-085938 A 5/2013
JP 3201196 U 11/2015
JP 6752215 B2 * 9/2020 ............. A61F 13/02
KR 20060102555 A * 9/2006 ........ A61M 37/0092
KR 101549086 B1 9/2015
WO WO-2008091878 A1 * 7/2008 ............. A61N 1/325
WO WO-2010010974 A1 * 1/2010 ........ A61M 37/0015
WO WO-2013096027 A1 * 6/2013 .............. A61P 17/00

OTHER PUBLICATIONS

International Search report in Japanese Application No. PCT/JP2017/004835 dated Apr. 11, 2017.
Office Action received in Japanese Application No. 2018-540883 dated Sep. 15, 2020.
Office Action received in Chinese Application No. 20170009631.1 dated May 6, 2021.
Office Action and Search report received in Chinese Application No. 201780009631.1 dated Aug. 31, 2020.
Office Action received in Indian Application No. 201847032662 dated Jul. 6, 2021.
Office Action U.S. Appl. No. 16/075,376 dated Sep. 22, 2021.
Office Action issued in corresponding Korean Patent Appl. No. 10-2018-7024497 dated Oct. 17, 2023.

* cited by examiner

FIG. 1

(Prior Art)

Prior Art

TRANSDERMAL PERMEANT APPLICATION DEVICE

This application is a continuation of U.S. application Ser. No. 16/075,376, filed on Aug. 3, 2018, which is the U.S. National Phase of International Application No. PCT/JP2017/004835, filed on Feb. 3, 2017, which claims the benefit of U.S. Provisional Application No. 62/291,752, filed Feb. 5, 2016, the disclosure of which are incorporated herein by reference in their entireties.

TECHNICAL FIELD

This invention relates to a device for transdermal application or delivery of a permeant through biological membrane or skin of a subject. More particularly, this invention relates to a transdermal permeant application device having a new positioning mechanism capable of preferably placing a patch on a target area of a skin surface of a subject, or on a target porated area (area enveloping many micropores formed in the skin) formed by a porator in a skin of a subject. The device may be called a transdermal permeant application or delivery system, depending on the embodiment thereof.

BACKGROUND ART

The stratum corneum, the outer horny layer of the skin, is chiefly responsible for the barrier properties of skin. Thus, it is this layer that presents the greatest barrier to transdermal flux of drugs or other molecules into the living body and of analytes out of the living body.

In recent years, transdermal delivery to the body has been a popular and efficacious method for delivering a limited number of permeants into an organism. Thus, various transdermal permeant delivery systems or devices have been developed. For example, PCT WO 2008-091878 (the disclosure of which is hereby incorporated by reference) describes a preferable transdermal permeant delivery system. As shown in FIG. 1 of the present application, system 100 of PCT WO 2008-091878 comprises at least an porator (disposable porating head) 120 to which a patch 110 is detachably attached and an applicator (reusable main device with a power source) 130 to which a porator 120 is connected. The patch 110 comprises an adhesive sheet 112 to be adhered to a skin surface and a reservoir 114 placed on the adhesive sheet the patch 110, a release liner covering an adhesive surface of the adhesive sheet 112 and the reservoir 114, and a casting sheet (supporting liner) to be detachably attached to the back-surface of the adhesive sheet are laminated (not explicitly shown in FIG. 1).

In use, a filament array (micro-heating elements) 122 in the porator 120 generates heat when supplied with energy (typically, electrical energy) from an applicator 130, and forms many micropores in the stratum corneum of a small area on the skin surface. Subsequent to the porating, the porated area is covered with the reservoir 114 of the patch 110, whereby permeant(s) are delivered into the body through the micropores.

FIG. 2 is a copy of an internet product advertisement of a transdermal permeant delivery system, which has improved functionality, operability and design (ornamentality) as compared to the system shown in FIG. 1. The advertisement is published as "TRANSDERMAL TECHNOLOGY EVOLUTION" in the web-site of Nitto Denko Technical Corporation. The system shown in FIG. 2 also comprises, like the system of FIG. 1, "APPLICATOR DEVICE" (having a power supply), "ASSEMBLED PORATOR", and "TRANSDERMAL PATCH" (adhesive sheet with reservoir). The cross section of the skin in the advertisement of FIG. 2 easily illustrates delivery of the drug in the reservoir through the micropores after placing "TRANSDERMAL PATCH" reservoir on the porated area.

In the systems of FIG. 1 and FIG. 2, to cover the whole porated area with the reservoir, the reservoir needs to be appropriately aligned on the porated area. However, an identification of the porated area by visual observation is unclear immediately after poration.

The size of the reservoir can be larger than that of the porated area to facilitate covering of the porated area. From the economical aspect and to avoid waste, too large size of the reservoir is not preferable. On the contrary, higher accuracy of alignment becomes necessary as the size of the reservoir becomes closer to the size of the porated area.

Therefore, various alignment mechanisms have been proposed in the conventional transdermal permeant delivery systems.

SUMMARY OF THE INVENTION

Problems to be Solved by the Invention

In the transdermal permeant delivery systems of FIG. 1 and FIG. 2, the basic principle for aligning the reservoir to a porated area is the same. FIG. 3 understandably shows the alignment operation in accordance with the principle.

As shown in FIG. 3 (*a*), a filament array 122 having micro-heating elements 124 is on the lower surface (objective-surface) of a porator 120 coupled with an applicator 130, and a patch 110 having an adhesive sheet 112 and a reservoir 114 is detachably set next to the filament array 122. A release liner covering the adhesive surface of the adhesive sheet and the reservoir, and a casting sheet for imparting rigidity are not shown for explanation. The adhesive sheet 112 is folded with the adhesive surface facing outside, and the reservoir 114 is placed at a given position on the adhesive surface facing upward (top adhesive surface). In a plane view observing FIG. 3 (*a*) from a side, the reservoir 114 and the filament array 122 are laid symmetrically in a reference to the adhesive folding line (symmetry line vertical to the face of Figure) 113, such that the reservoir 114 can be aligned to the porated area. The symmetry line 113 is also shown in FIG. 1.

As shown in FIG. 3, (b), porator 120 is pressed against skin surface 140 to start porating, and a porated area 152 having micro-pores 154 can be formed. The thick arrow indicates the moving direction of the system. At this time, the bottom adhesive surface 112*b* of the folded adhesive sheet 112 adhered to the skin surface 140.

As shown in FIG. 3, (c), when the system is separated upward from the skin surface after completion of porating, the patch 110 remains on the skin surface.

Finally, as shown in FIG. 3, (d) with a thick arrow, the folded adhesive sheet 112 is unfolded, the reservoir 114 is pivotally turned 180 degrees, around the symmetry line 113, as a result of which the reservoir 114 is positioned aligned on the porated area 152.

The alignment mechanism shown in FIG. 3 is preferable since it can appropriately align the reservoir of a patch on a porated area. However, the present inventor has found the following points to be improved in such alignment mechanism.

First of all, a system having the above-mentioned alignment mechanism requires the following many steps (a)-(h) in actual use:

(a) clipping on the porator to the applicator,
(b) removing a bottom release liner covering the bottom adhesive surface,
(c) applying the system to skin,
(d) porating,
(e) removing the applicator, while leaving the patch (comprising folded adhesive sheet and the reservoir) on the skin surface,
(f) unfolding the adhesive sheet pivotally, and placing the reservoir on the porated area,
(g) smoothing out the adhesive sheet,
(h) removing a casting sheet covering a back face of the adhesive sheet.

In addition, the step (f) above relies on the user to correctly unfold the adhesive sheet and place the reservoir onto the porated area. This is a critical user-related risk which if not performed correctly could lead to:

1. Misplacement of the reservoir (not properly unfolded over the porated area, leading to underdose);
2. Delayed placement of the reservoir (inefficacy of poration, leading to underdose);
3. Direct exposure of the active drug compound to touch (displacement or contamination of the drug compound);
4. Prolonged direct exposure of the active drug compound to ambient environment (displacement or contamination of the drug compound).

It might be not clear to the patient how many steps are left in the process and whether or not the process is complete.

Furthermore, the adhesive sheet is held together by a casting sheet that is difficult to remove and can sometimes lead to the user removing the adhesive sheet with the reservoir altogether.

The present invention aims to provide a transdermal permeant application or delivery device having a new positioning or aligning mechanism capable of appropriately placing a patch on a target area of a skin surface of a subject. The present invention further aims to solve the above-mentioned problems, and provide a transdermal permeant application or delivery device having a new positioning or aligning mechanism capable of appropriately placing a patch reservoir on a porated area.

Solution to the Problems

The main constitution of the present invention is as follows.

(1) A transdermal permeant application device comprising:

a patch application support;

a patch having an adhesive area, the adhesive area having a first part and a second part; and an intervening release liner provided between the patch application support and the patch, the intervening release liner covering the second part of the adhesive area of the patch, and getting away from the patch and turning over, and being fixed to the patch application support;

whereby, under a situation in use where the first part of the adhesive area of the patch adheres to a skin surface, the patch application support is slidable along the skin surface while peeling the intervening release liner from the second part of the adhesive area of the patch to adhere to the skin surface.

(2) The transdermal permeant application device of the above-mentioned (1), wherein the patch application support further comprises a spatula which extends to a position laterally away from the patch application support, such that, when in use, the patch application support slides along the skin surface, and the spatula follows to slide on the patch, while pressing the patch against the skin surface.

(3) The transdermal permeant application device of the above-mentioned (1), further comprising a reusable body, wherein the patch application support, the patch, and the intervening release liner are replaceably attached to the reusable body.

(4) The transdermal permeant application device of the above-mentioned (3), wherein the reusable body further comprises a spatula which extends to a position laterally away from the patch application support, such that, when in use, the reusable body and the patch application support slide along the skin surface, and the spatula follows to slide on the patch, while pressing the patch against the skin surface.

(5) The transdermal permeant application device of the above-mentioned (3), wherein the patch application support further comprises a spatula which extends to a position laterally away from the patch application support, such that, when in use, the patch application support slides along the skin surface, and the spatula follows to slide on the patch, while pressing the patch against the skin surface.

(6) The transdermal permeant application device of the above-mentioned (3), wherein the reusable body further comprises a roller which is placed on a position laterally away from the patch application support, such that, when in use, the reusable body and the patch application support slide along the skin surface, and the roller follows to roll on the adhesive sheet, while pressing the patch against the skin surface.

(7) The transdermal permeant application device of the above-mentioned (1), wherein the patch is bent at a predetermined inner angle 01 (0 degrees<01<180 degrees) with the adhesive area facing outside, and the bending line thereof divides the adhesive area into the first part and the second part, the first part is placed on a position laterally away from the patch application support, to adhere to the skin surface when in use, the second part stands up at the inner angle 01, with the adhesive area facing the patch application support, the intervening release liner is provided between the patch application support and patch, the intervening release liner covering the second part, and being fixed to the patch application support, whereby, under a situation in use where the first part of the adhesive area of the patch adheres to the skin surface, the patch application support is slidable along the skin surface while peeling the intervening release liner from the second part of the adhesive area of the patch to adhere to the skin surface.

(8) The transdermal permeant application device of the above-mentioned (7), further comprising a fork to hold the patch at a given position in relation to the patch application support, wherein the fork comprises:

two claws to be fitted in the patch application support; and a flat part under which an upper side of the first part of the adhesive area is attached directly or via a casting sheet.

(9) The transdermal permeant application device of the above-mentioned (1), further comprising a porating element, wherein the porating element is provided in or on the patch application support, and the porating element is adapted to form at least one pore in the skin surface, whereby, under a situation in use where the first part of the adhesive area of the patch adheres to the skin surface and the porating element forms at least one pore in the skin surface, the patch application support with the porating element is slidable along the skin surface while peeling the intervening release liner to allow the patch to alignedly cover the porated area.

(10) The transdermal permeant application device of the above-mentioned (9), wherein the porating element is selected from a group consisting of:

one or more elements capable of delivering thermal energy via direct contact to the skin to cause ablation to form the skin;

one or more elements capable of delivering electrical energy via direct contact to the skin to cause ablation to form the skin;

one or more electro-mechanical actuator, one or more lancets;

one or more micro-needles;

one or more sonic energy ablator;

one or more laser ablation elements;

one or more physical ablation elements; and one or more fluid jet puncturers.

(11) The transdermal permeant application device of the above-mentioned (10), further comprising an applicator as a reusable body having a driving source therein, wherein the patch application support, the patch, and the intervening release liner are replaceably attached to the applicator, and the driving source is adapted to drive the porating element to form at least one pore in the skin surface.

(12) The transdermal permeant application device of the above-mentioned (9), further comprising an applicator as a reusable body having a power source therein, wherein the patch application support, the patch, and the intervening release liner are replaceably attached to the applicator, and the porating element is adapted to receive electric power from the power source to form at least one pore in the skin surface by delivering thermal energy via direct contact to the skin to cause ablation to form the skin.

(13) The transdermal permeant application device of the above-mentioned (12), further comprising:

a porator backing; and a porator tab as the patch application support, wherein the porator tab is a band-shaped plate with one end thereof fixed to the porator backing, the porator tab comprising:

an objective-surface facing outer side such that, when in use, the objective-surface contacts the skin surface of a subject;

a back-surface on the opposite side of the objective-surface; and one or more filaments as the porating element in a porating area in the objective-surface of the porator tab, wherein the one or more filaments generates heat to form one or more micropores in the skin of the subject, and wherein the patch is placed on a back-surface side of the porator tab, the patch having an adhesive sheet and a reservoir placed on an adhesive surface of the adhesive sheet, the reservoir releasably contains a permeant to be delivered through the micropores, and is alignedly placed on the back at a position corresponding to the porating area, and the adhesive surface of the adhesive sheet faces the subject side, and the adhesive sheet comprises:

the first part extending from the free end and both longitudinal side edges of the porator tab, to adhere to the skin surface; and the second part which is a remaining part, not extending from the porator tab, and wherein the intervening release liner is provided between the porator tab and the patch, the intervening release liner covering the adhesive surface of the second part and the reservoir, and getting away from the patch, and turns over, and is fixed to the porator tab, whereby, under a situation in use where the first part of the adhesive sheet adheres to the skin surface, the porator tab is slidable along the skin surface to the outside of the covering area of the adhesive sheet, while peeling the intervening release liner from the patch to allow the reservoir to alignedly cover the porated area, and the adhesive surface of the second part to adhere to the skin surface.

(14) The transdermal permeant application device of the above-mentioned (13), wherein the porator backing further comprises a spatula which extends to a position laterally away from the porator tab, such that, when in use, the porator tab slides towards its fixed end side along the skin surface, and the spatula follows to slide on the adhesive sheet, while pressing the adhesive sheet against the skin surface to smooth the adhesive sheet.

(15) The transdermal permeant application device of the above-mentioned (13), wherein the applicator further comprises a spatula which extends to a position laterally away from the porator tab, such that, when in use, the porator tab slides towards its fixed-end side along the skin surface, and the spatula follows to slide on the adhesive sheet, while pressing the adhesive sheet against the skin surface to smooth the adhesive sheet.

(16) The transdermal permeant application device of the above-mentioned (13), wherein the applicator further comprises a roller which is placed on a position laterally away from the porator tab, such that, when in use, the porator tab slides towards its fixed end side along the skin surface, and the roller follows to roll on the adhesive sheet, while pressing the adhesive sheet against the skin surface to smooth the adhesive sheet.

(17) The transdermal permeant application device of the above-mentioned (13), wherein the applicator further comprises a vacuum source, and the porator tab comprises one or more paths to apply a vacuum sucking force from the vacuum source to the skin surface.

(18) The transdermal permeant application device of the above-mentioned (12), further comprising:

a porator backing with the patch application support, wherein the patch application support comprising:

an objective-surface facing outer side such that, when in use, the objective-surface contacts a skin surface of a subject; and one or more filaments as the porating element in a porating area in the objective-surface, wherein the one or more filaments generates heat to form one or more micropores in the skin of the subject, and wherein the patch is detachably attached to the porator backing or the applicator, and the patch has an adhesive sheet and a reservoir placed on an adhesive surface of the adhesive sheet, the reservoir releasably contains a permeant to be delivered through the micropores, the adhesive sheet is bent at a predetermined inner angle 01 (0 degrees<01<180 degrees) with the adhesive surface facing outside, and the bending line thereof divides the adhesive sheet into the first part and the second part, the first part is placed on a position laterally away from the porator backing, to adhere to the skin surface when in use, the bending line is located on the side closer to the porating area in the outer circumference of the first part, the second part stands up at the inner angle 01, with the adhesive surface facing the porating area, the reservoir is placed at a given position on the adhesive surface of the second part, such that the reservoir and the porating area are symmetrically corresponding with the bending line, and the intervening release liner is provided between the patch application support and patch, the intervening release liner covering the adhesive surface of the second part and the reservoir, and being fixed to the patch application support or the porator backing, whereby, under a situation in use where the first part of the adhesive sheet adheres to the skin surface, the applicator and the porator backing with the patch application support are slidable along the skin surface to outside of the area to be covered with the adhesive sheet, while peeling the intervening release liner from the patch to allow the reservoir to alignedly cover the porated area, and the adhesive surface of the second part to adhere to the skin surface.

(19) The transdermal permeant application device of the above-mentioned (18), wherein the applicator further comprises a vacuum source, and the patch application support comprises one or more paths to apply a vacuum sucking force from the vacuum source to the skin surface.

(20) The transdermal permeant application device of the above-mentioned (18), further comprising a fork to hold the patch at a given position in relation to the patch application support, wherein the fork comprises:

two claws to be fitted in the porator backing; and a flat part under which an upper side of the first part of the adhesive sheet is attached directly or via a casting sheet.

BRIEF DESCRIPTION OF DRAWINGS

Figure 1:
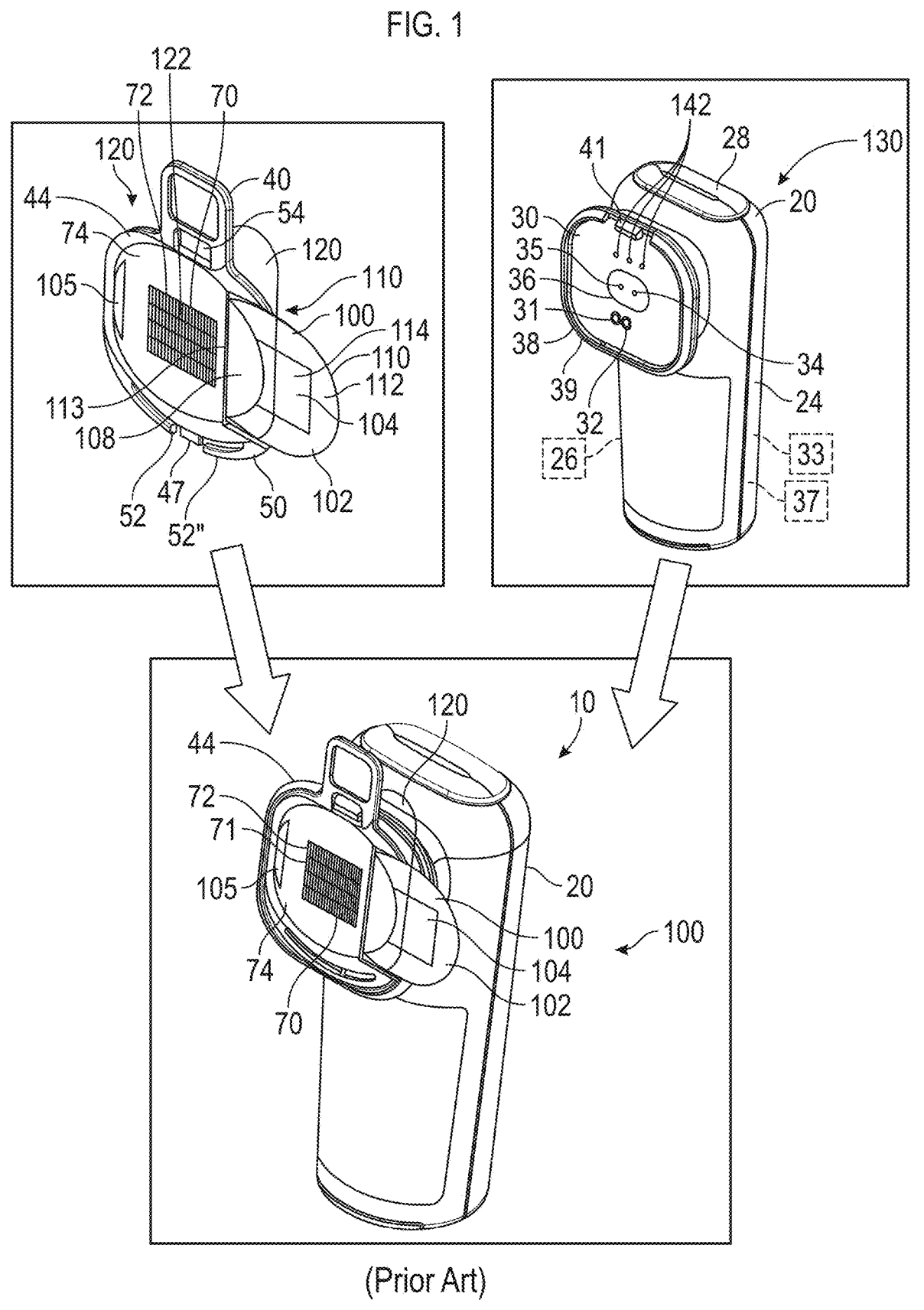

FIG. 1 shows one embodiment of a conventional preferable transdermal permeant delivery system.

FIG. 8 (*a*) is the device viewed from obliquely below, and FIG. 8 (*b*) is the device viewed from obliquely above.

FIG. 14 (*a*) shows the porator-patch assembly viewed from obliquely below, FIG. 14 (*b*) shows the porator-patch assembly viewed from obliquely above, and FIG. 14 (*c*) shows a cross section of the portator-patch assembly viewed from obliquely above.

FIG. 17 is a sectional view showing a preferable embodiment of the spatula and an action thereof in a perspective view. FIG. 17(*b*)-(*d*) are a schematic view showing the intervening release liner remains attached to the porator tab as it is pulled away, progressively exposing the reservoir to the porated area of the skin, and the adhesive second part to the periphery of the porated area.

FIG. 22 (*a*) is the porator backing viewed from obliquely below, and FIG. 22 (*b*) is the porator backing viewed from obliquely above.

FIG. 27 (*a*) is the applicator with interface viewed from obliquely below, and FIG. 27 (*b*) is a sectional view of interface coupled with the porator backing.

FIG. 28 (*a*) is the porator backing viewed from obliquely below, and FIG. 28, (b) is the porator backing viewed from obliquely above.

FIG. 29 (*a*) is the fork with patch viewed from obliquely above, and FIG. 29 (*b*) is the fork inserted into the porator backing viewed from obliquely below.

DESCRIPTION OF EMBODIMENTS

The present invention is explained below by way of preferable embodiments.

Figure 2:
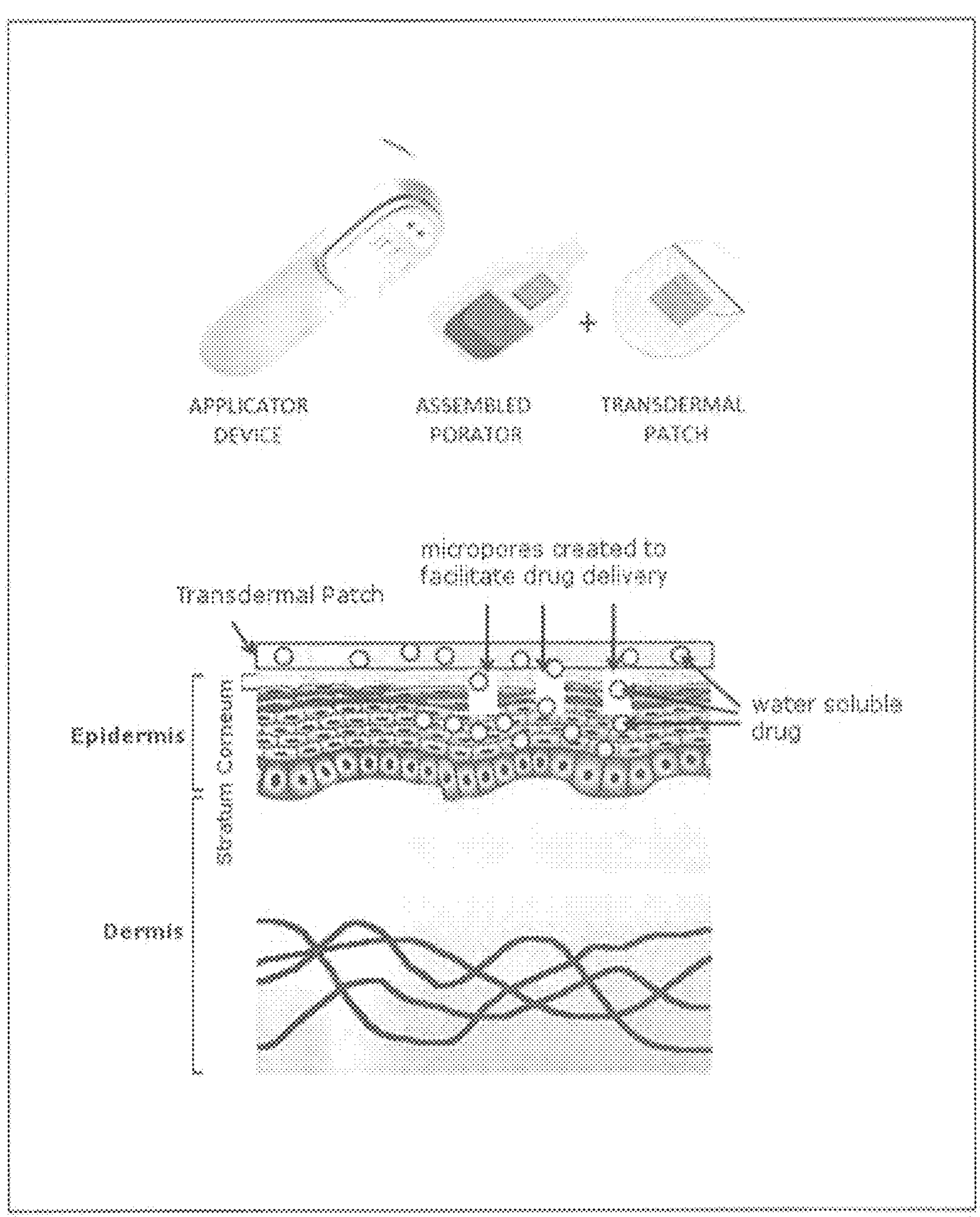
FIG. 2 is a copy of an internet advertisement showing the conventional preferable transdermal permeant delivery system.
Figure 3:
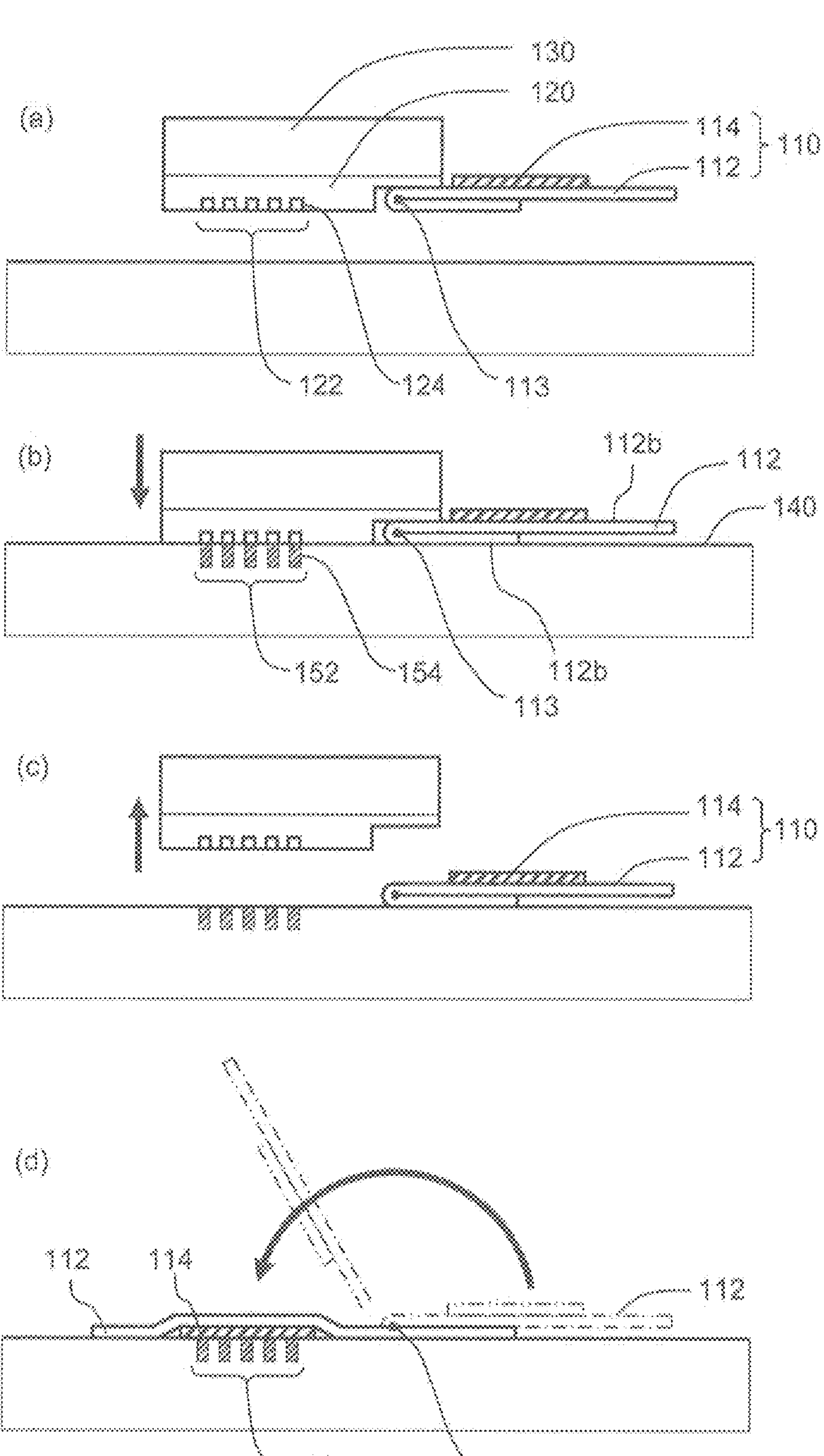
FIG. 3(*a*)-(*d*) illustrates an alignment mechanism of porated area and reservoir in a conventional system.
Figure 4:
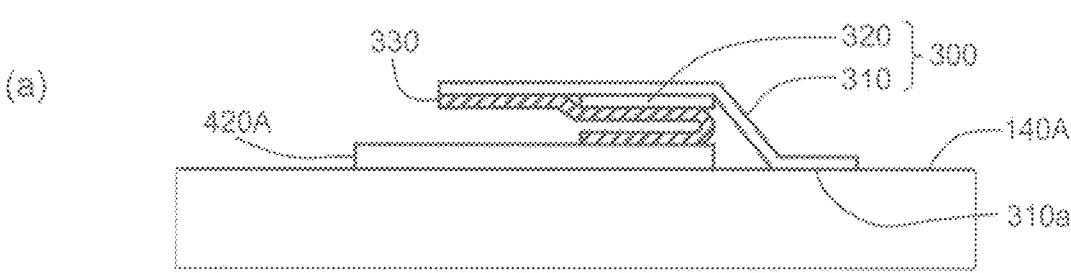
FIG. 4(*a*)-(*e*) are schematic views illustrating the principle of positioning in an embodiment of the present invention.
Figure 4:
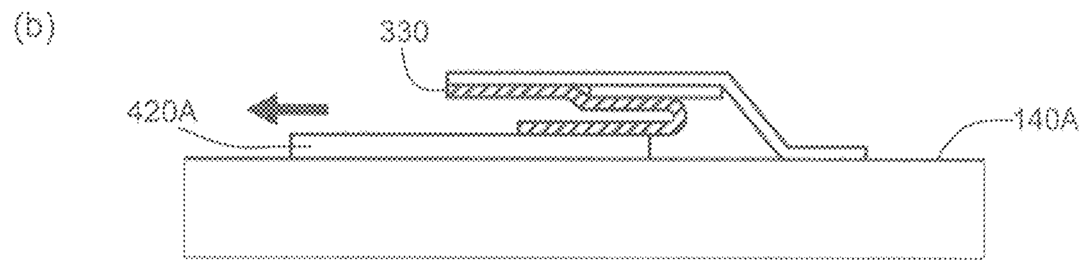
Figure 4:
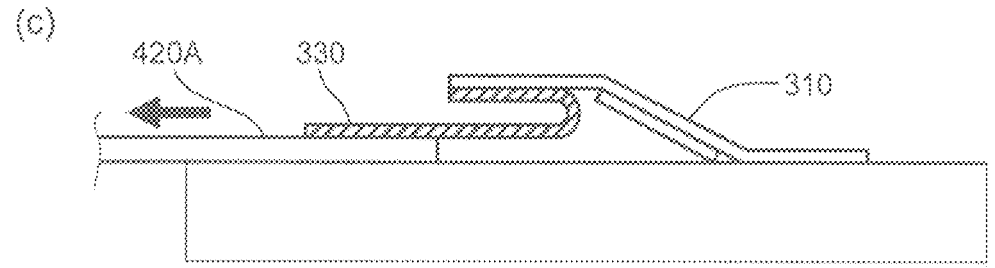
Figure 4:
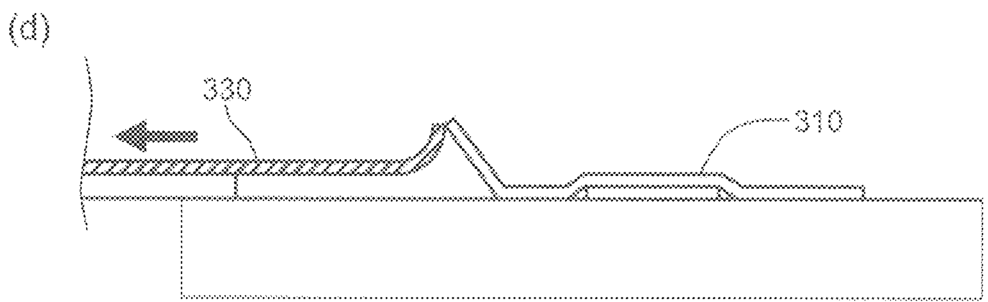
Figure 4:
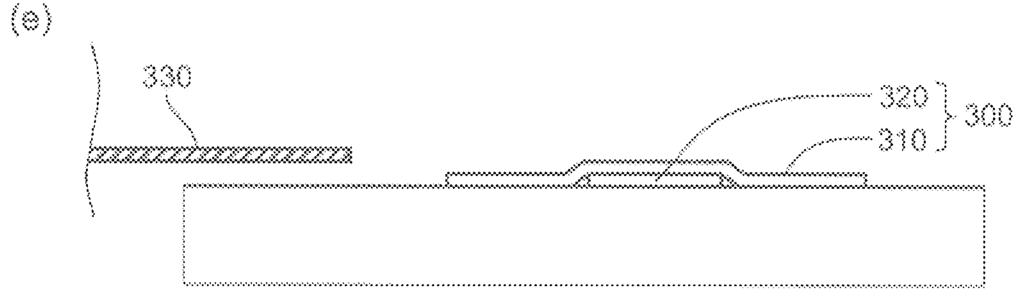
Figure 7:
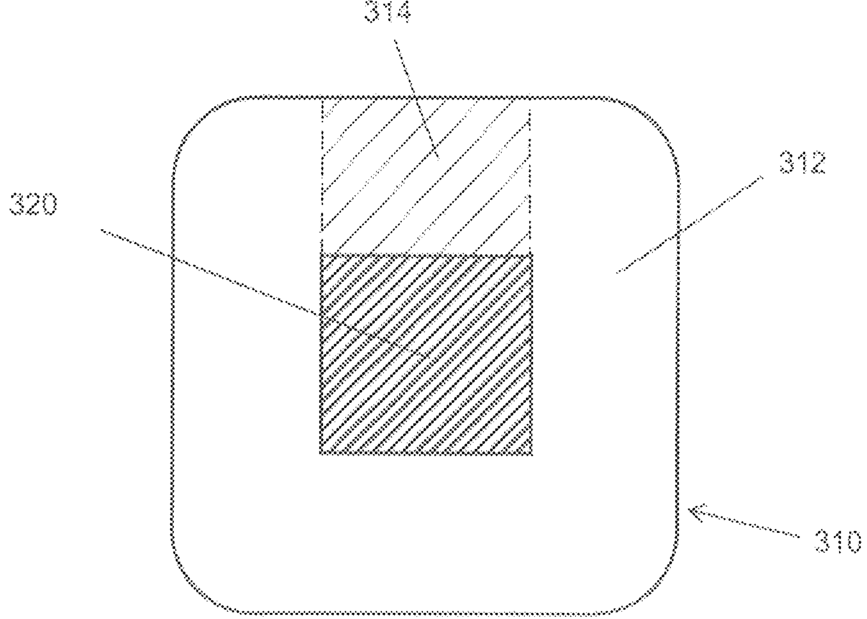
FIG. 7 is a plan view showing one embodiment of the patch of the first embodiment of the present invention.

As shown in FIG. 4, the transdermal permeant application device (hereinafter to be also referred to as the device) of the present invention comprises at least a patch application support 420A, a patch 300, and an intervening release liner 330. In the embodiment of FIG. 4, the patch application support 420A preferably has a shape of a plate, particularly preferably a tab-shaped plate, a strip-shaped plate, or a belt-shaped plate. In FIG. 4, the patch 300 comprises an adhesive sheet 310 and a reservoir 320 placed on an adhesive area (adhesive surface) 310*a* of the adhesive sheet 310. However, the patch may be a single sheet like a plaster. As shown in FIG. 7, the patch 300 has an adhesive area 310*a* having a first part 312 and a second part 314. When the patch 300 is a single sheet and does not have a topical reservoir, the area of the reservoir 320 in FIG. 7 may belong to the second part 314.

The intervening release liner 330 is provided between the patch application support 420A and the patch 300. The intervening release liner 330 covers the second part 314 of the adhesive area of the patch 300, and turns over, preferably curls around while getting away from the patch, and is fixed to the patch application support 420A, via attaching feature (end part). Due to such configuration, as shown in FIG. 4 (*a*)-(*e*), under a situation in use where the first part of the adhesive area of the patch 300 adheres to a skin surface 140A, the patch application support 420A is slidable (not lifts) along the skin surface 140A while peeling the intervening release liner 330 from the second part of the adhesive area of the patch 300 to adhere to the skin surface 140A. Thus the patch 300 easily and preferably covers the target area (which may or may not be a porated area). As described below, the usefulness of the positioning and aligning mechanism of the present invention becomes more prominent in an embodiment containing a patch on a porated area.

In a preferable embodiment, the device of the present invention comprise a reusable body. In the embodiment, the patch application support 420A, the patch 300, and the intervening release liner 330 are replaceably attached to the reusable body. For example, in the embodiment shown in FIG. 8, the reusable body is illustrated as an applicator 210 having a power source (not shown) therein. However, in an embodiment without porating, the power source may be absent, and the reusable body (such as, the applicator 210 in FIG. 8 or the applicator 250 in FIG. 25) may be a preferable housing to grip. The shape and size of the housing to grip can be appropriately determined in consideration of the operability or handleability.

Figure 8:
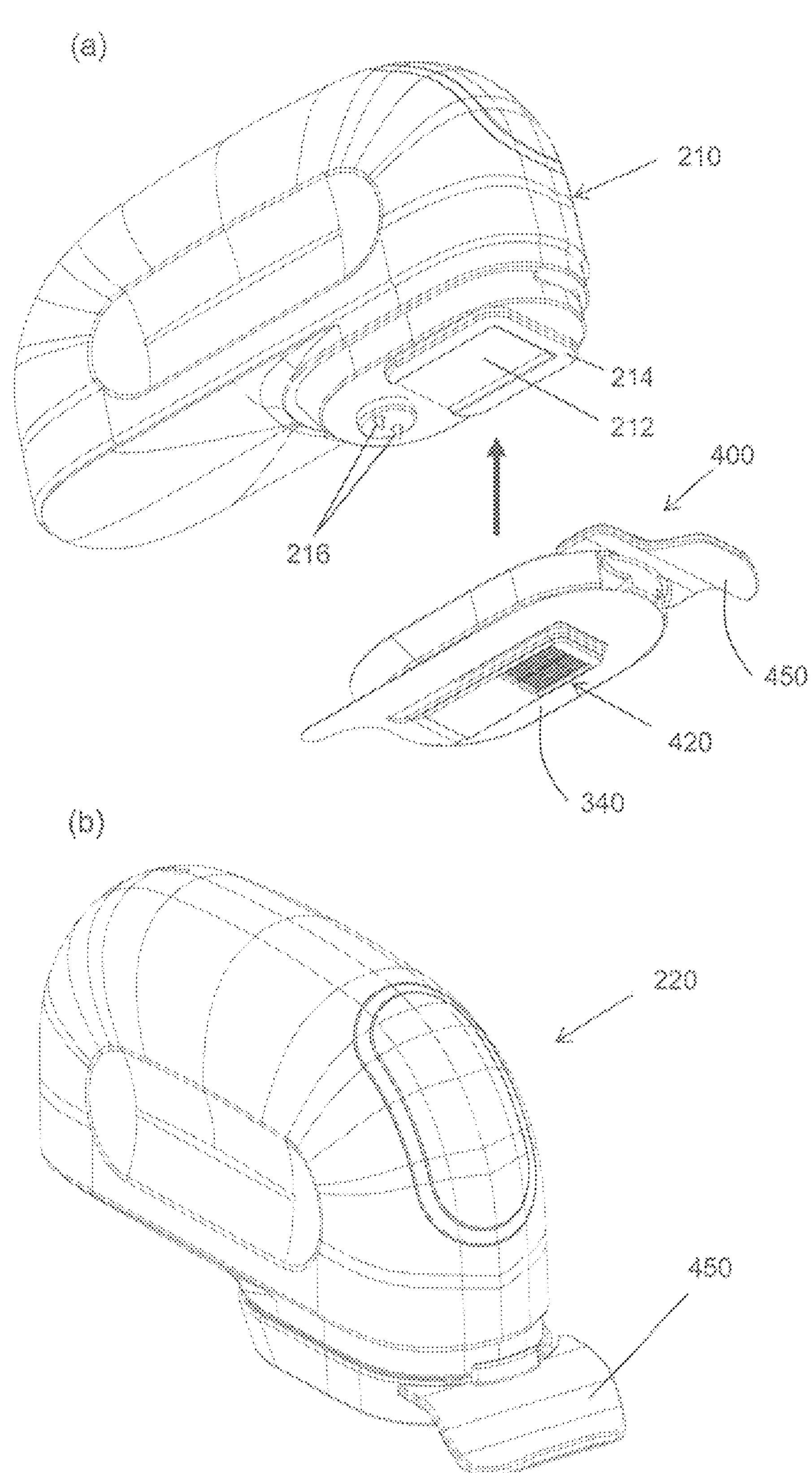
FIG. 8 is a perspective view showing one embodiment of preferable appearance of the device of the first embodiment of the present invention.
Figure 16:
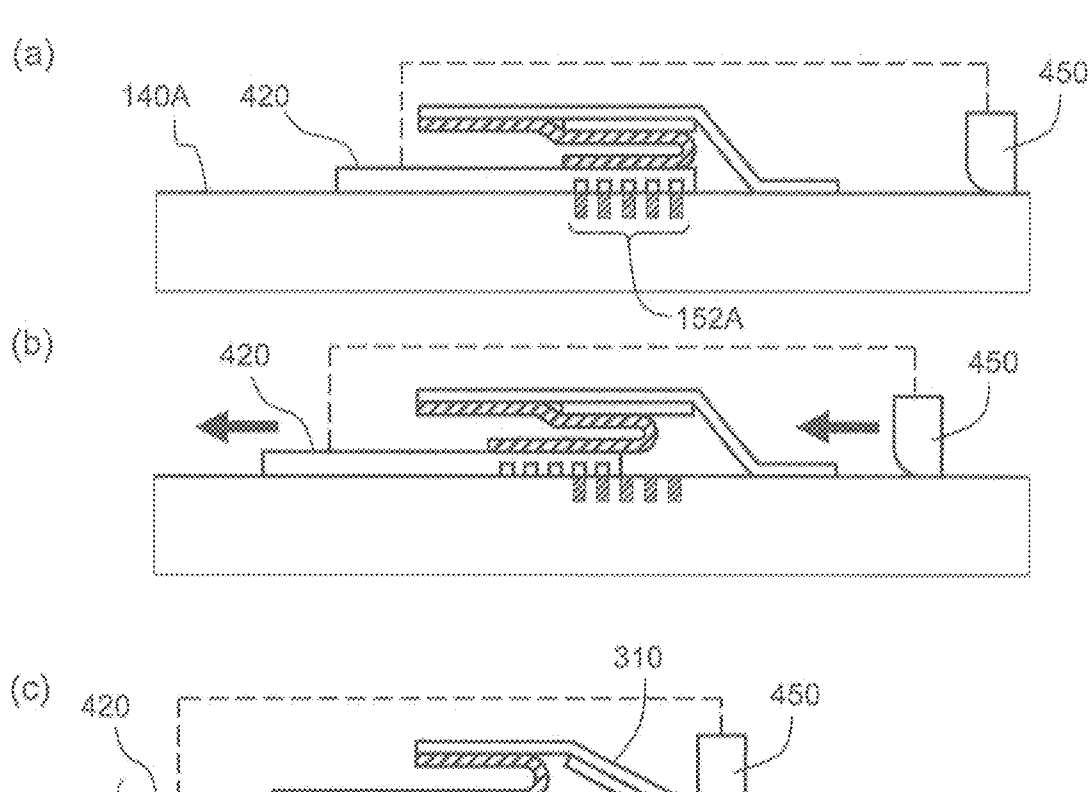
FIG. 16(*a*)-(*e*) are schematic views showing an action of the spatula in the first embodiment of the present invention.
Figure 16:
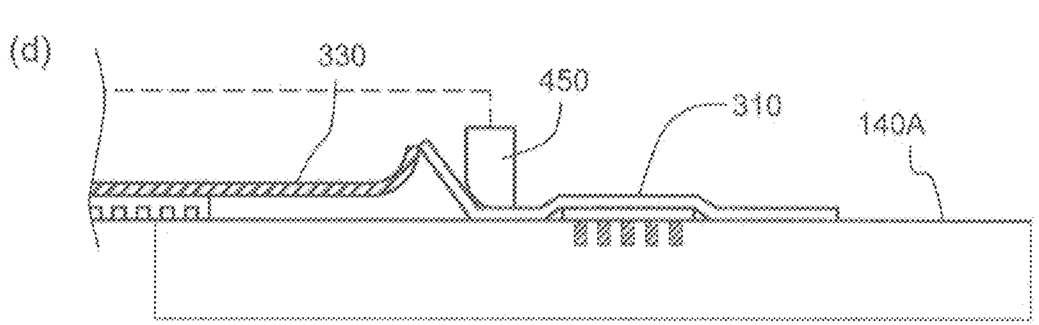
Figure 16:
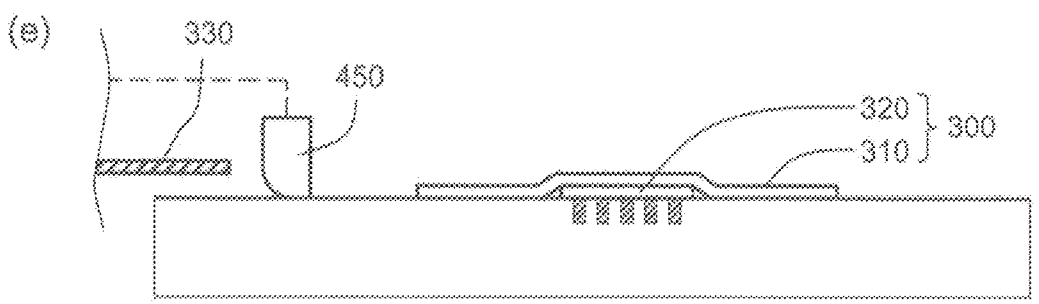

In a preferable embodiment, the patch application support 420A comprises a spatula 450 (as shown in FIGS. 8 and 16). Alternatively, the spatula may be provided on the reusable body. The spatula is explained in detail in the below-mentioned embodiment comprising a porator.

Figure 20:
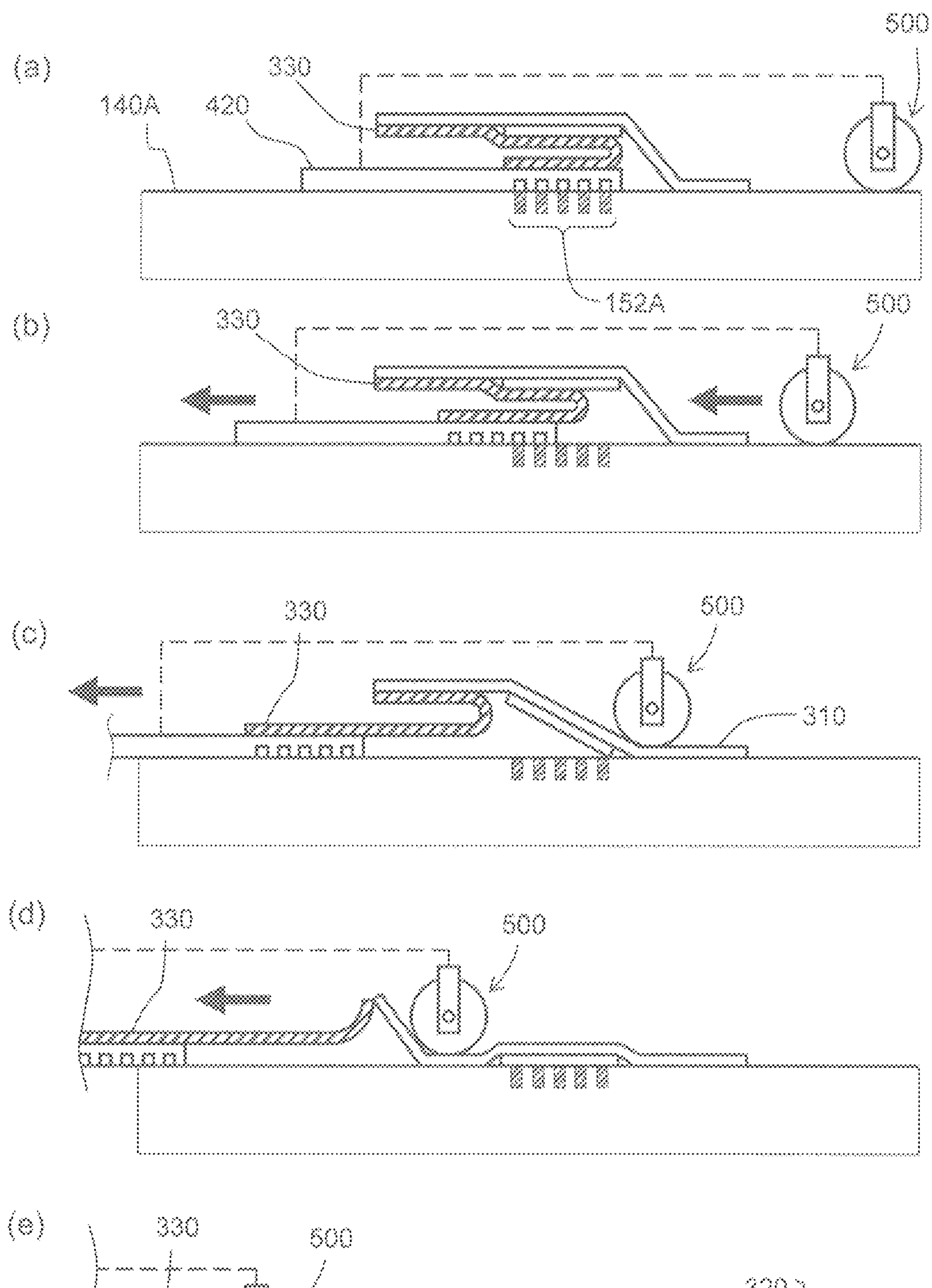
FIG. 20(*a*)-(*e*) are schematic views showing the action of a roller in the first embodiment of the present invention.
Figure 23:
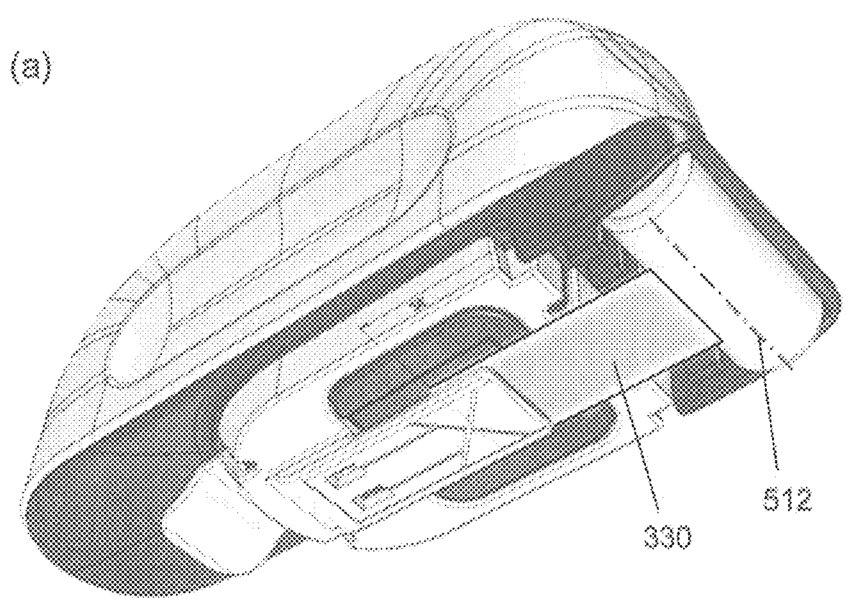
FIG. 23(*a*)-(*b*) shows the appearance of the device having a roller and the action of the roller.
Figure 23:
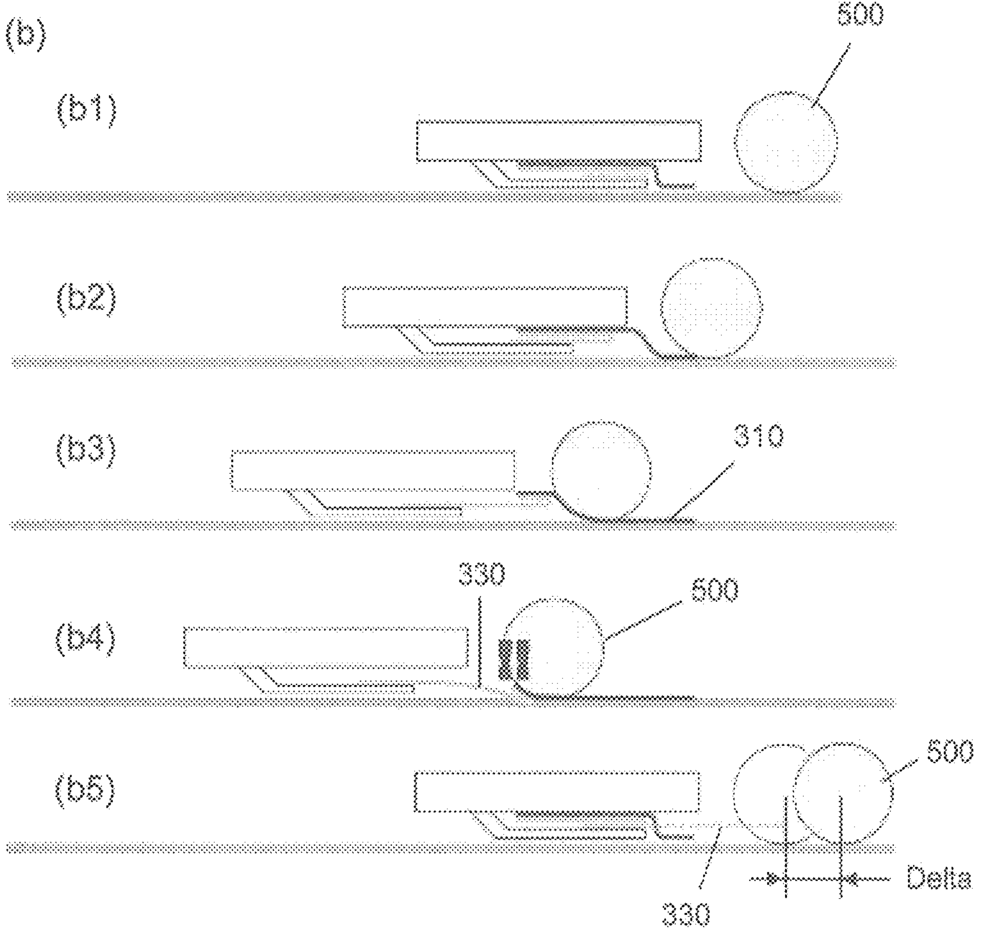

Also, in a preferable embodiment, the reusable body may comprise a roller 500 (as shown in FIGS. 20 and 23) instead of the spatula. The roller is explained in detail in the below-mentioned embodiment comprising a porator.

Figure 5:
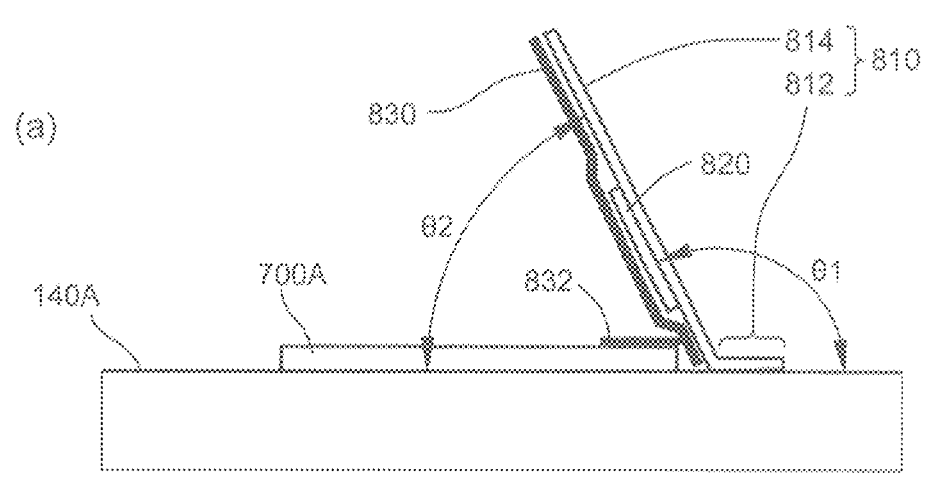
FIG. 5(*a*)-(*d*) are schematic views illustrating the principle of positioning in another embodiment of the present invention.
Figure 5:
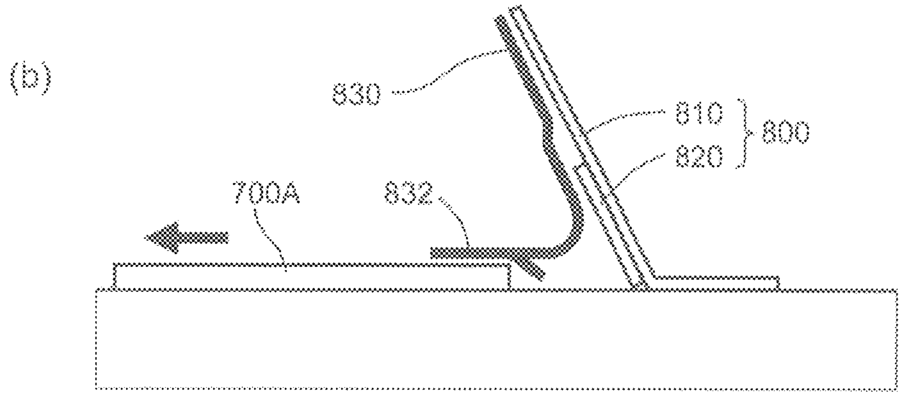
Figure 5:
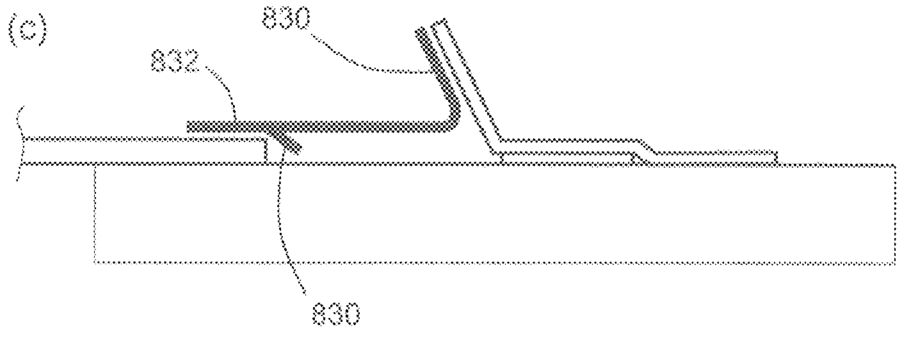
Figure 5:
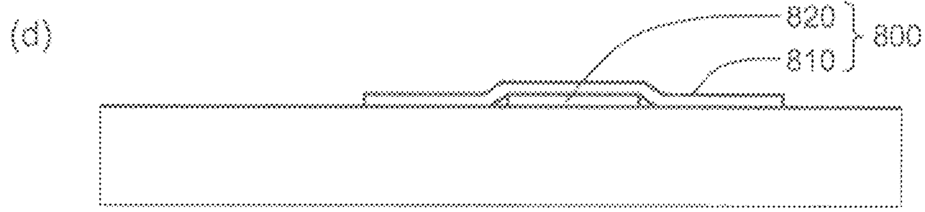

In a preferable embodiment, as shown in FIG. 5, the patch 800 is bent at a predetermined inner angle θ1 (0 degrees<θ1<180 degrees) with the adhesive area facing outside. The bending line thereof divides the adhesive area (adhesive sheet 810) into the first part 812 and the second part 814. The first part 812 is placed on a position laterally away from the patch application support 700A, to adhere to the skin surface 140A when in use. The second part 814 stands up at the inner angle θ1, with the adhesive area facing the patch application support 700A. In FIG. 5, the patch 800 comprises an adhesive sheet 810 and a reservoir 820 placed on an adhesive surface of the adhesive sheet 810, wherein the patch may be a single sheet like a plaster. When the patch 800 is a single sheet and does not have a topical reservoir, the area occupied by the reservoir 820 in FIG. 5 may belong to the second part 814.

Figure 25:
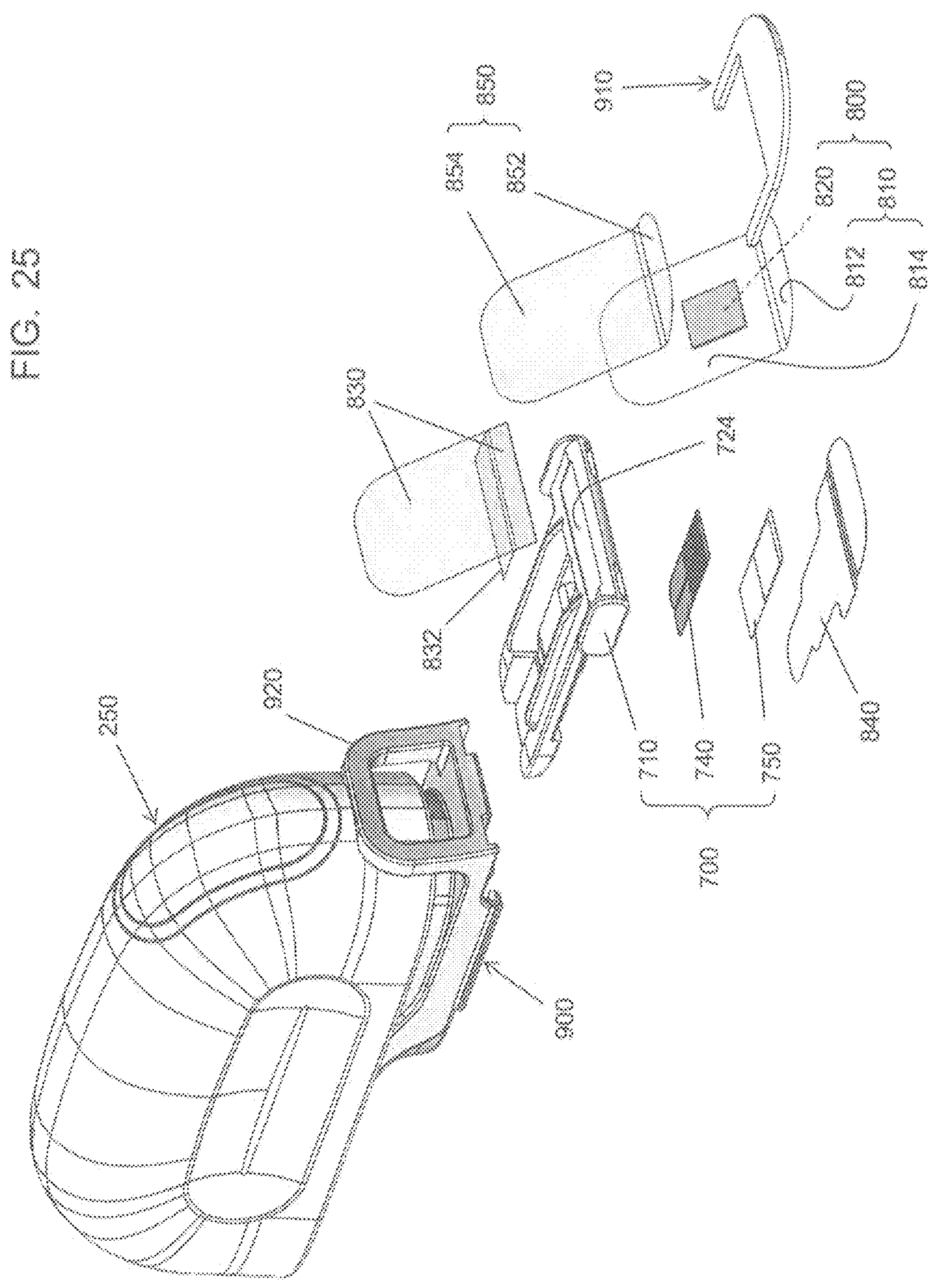
FIG. 25 an exploded schematic view of the porator-patch assembly in Example of the second embodiment of the present invention.
Figure 29:
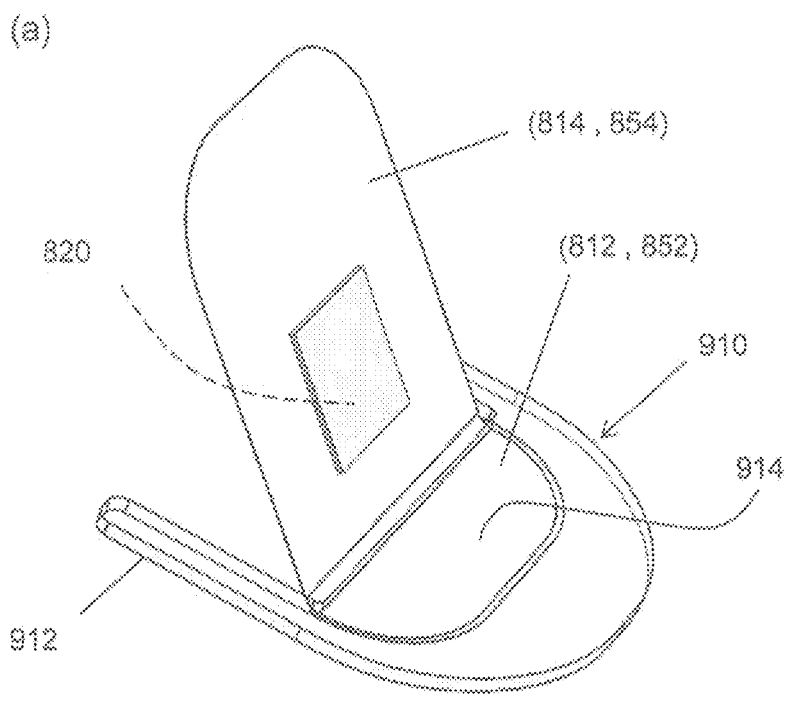
FIG. 29 is a perspective view showing a part (fork) in the second embodiment of the device of the present invention.
Figure 29:
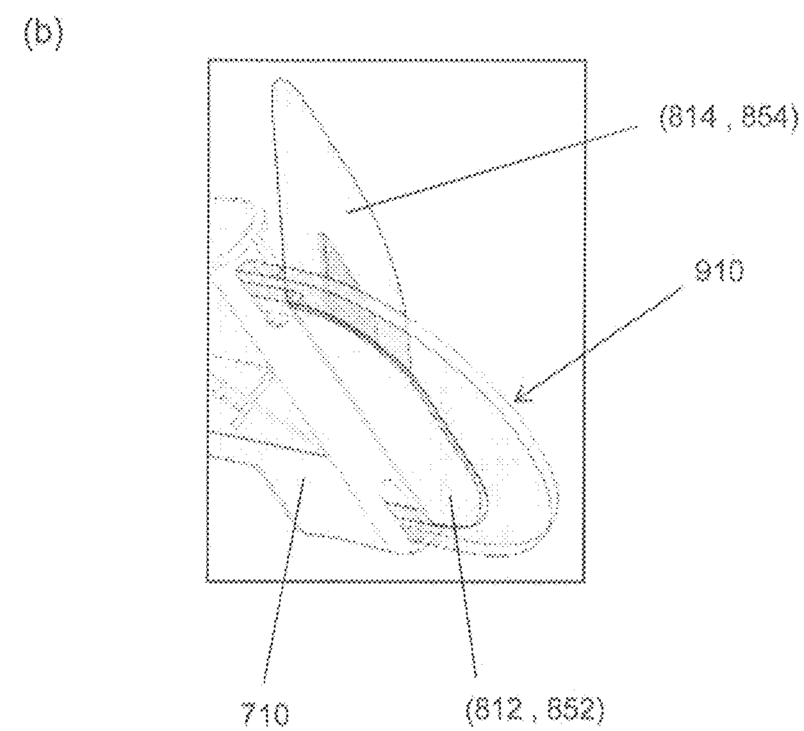

The intervening release liner 830 is provided between the patch application support 700A and patch 800. The intervening release liner 830 covers the second part 814, and being fixed to the patch application support 700A, via an attaching feature 832. The attaching feature may be a part branching out from the intervening release liner 830 or a bent end part of the intervening release liner 830. Due to such configuration, as shown in FIG. 5 (*a*)-(*d*), under a situation in use where the first part 812 of the patch 800 adheres to the skin surface 140A, the patch application support 700A is slidable along the skin surface 140A while peeling the intervening release liner 830 from the second part 814 of the adhesive area of the patch 800 to adhere to the skin surface 140A. In an embodiment shown in FIG. 5, the device may further comprise a fork as shown in FIGS. 25 and 29. The fork is explained in detail in the below-mentioned embodiment comprising a porator.

The embodiments shown in FIGS. 4 and 5 have an intervening release liner as a common special feature. The intervening release liner covers a part (second part) of the adhesive surface of the patch, and the attaching feature is fixed to the patch application support via attaching feature.

In a preferable embodiment, the device further comprises a porating element. The porating element is provided in or on the patch application support, and the porating element is adapted to form at least one pore in the skin surface. The usefulness of the positioning and aligning mechanism of the present invention becomes more remarkable in an embodiment wherein a patch is configured on the porated area, as described below.

While the porating element is not particularly limited, for example, the following can be mentioned: one or more elements capable of delivering thermal energy via direct contact to the skin to cause ablation to form the skin; one or more elements capable of delivering electrical energy via direct contact to the skin to cause ablation to form the skin; one or more electro-mechanical actuator, one or more lancets; one or more micro-needles; one or more sonic energy ablator; one or more laser ablation elements; one or more physical ablation elements; and one or more fluid jet puncturers. These porating elements may be used in combination.

Also, in a preferable embodiment, the device may comprise an applicator as the reusable body having a driving source therein. The patch application support, the patch, and the intervening release liner are replaceably attached to the applicator, and the driving source is adapted to drive the porating element to form at least one pore in the skin surface. For example, the driving source is adapted to provide appropriate energy (according to the porating element), such as, heat energy, electric energy, electromagnetic energy (including light energy), sound energy, ultrasonic energy, force (particularly pushing force), air flow, fluid flow, or a combination of these.

In a preferable embodiment, the porating element is adapted to receive electric power from the power source to form at least one pore in the skin surface by delivering thermal energy via direct contact to the skin to cause ablation to form the skin. Preferably, the porating element is a filament or a filament array. Conventional techniques may be referred to for the structure of filament array and porating technique using same.

In the examples of the present invention shown below, the device comprises a filament array as the porating element provided in or on the patch application support. Also the device comprises an applicator as the reusable body, and the applicator contains an electric power source therein for the filament array. And a reservoir of the patch can be preferably aligned on a porated area by the common alignment mechanism of the present invention.

The examples can be roughly divided into the following two embodiments based on the positions of the patch.

Figure 6:
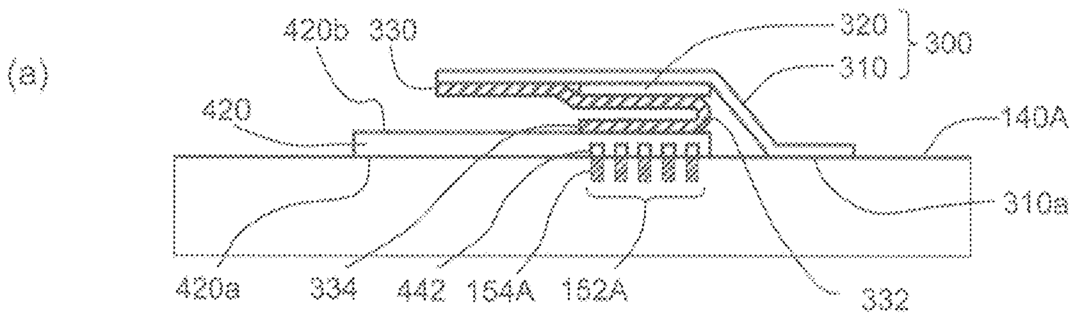
FIG. 6(*a*)-(*e*) are schematic views illustrating the principle of positioning (or alignment) in the first embodiment of the present invention.
Figure 6:
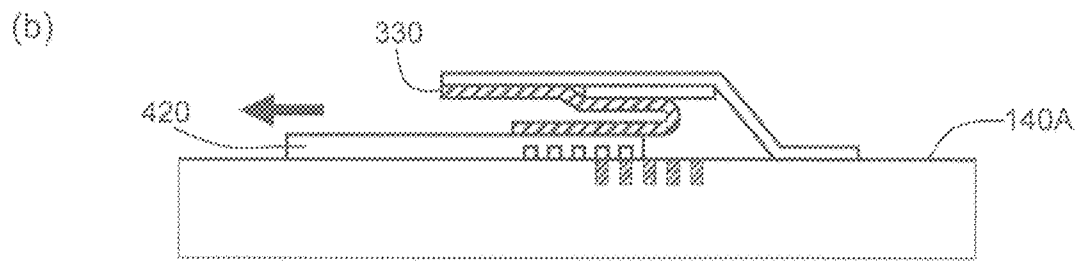
Figure 6:
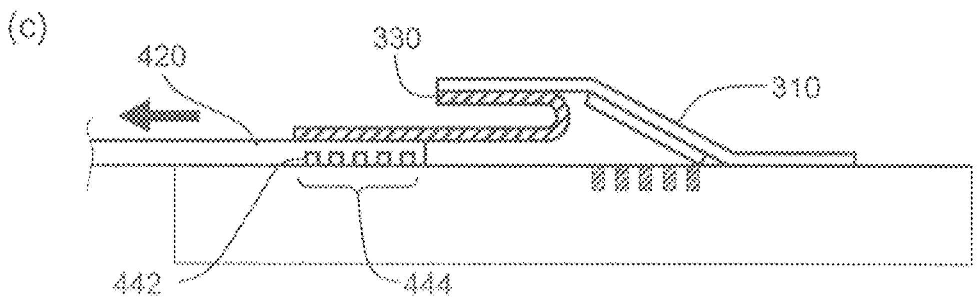
Figure 6:
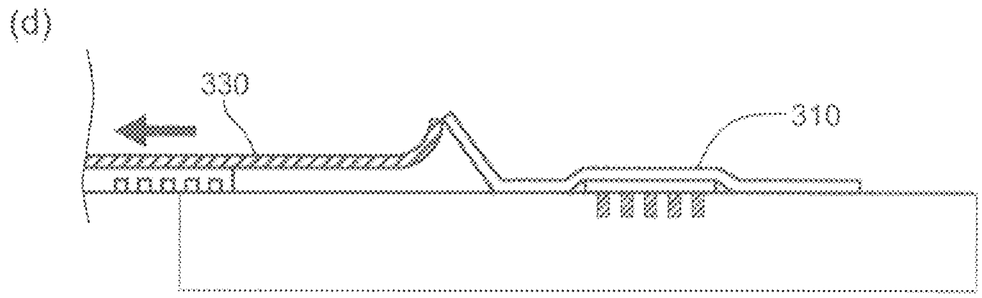
Figure 6:
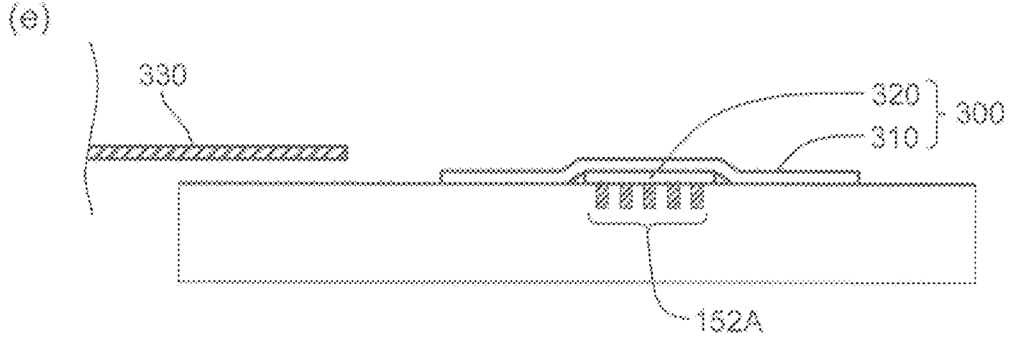

In the first embodiment, as shown in FIG. 6, the patch is positioned in the back of (namely, right over) the porating area, the adhesive sheet is spread (not folded), and maintained in parallel to the objective-surface.

Figure 24:
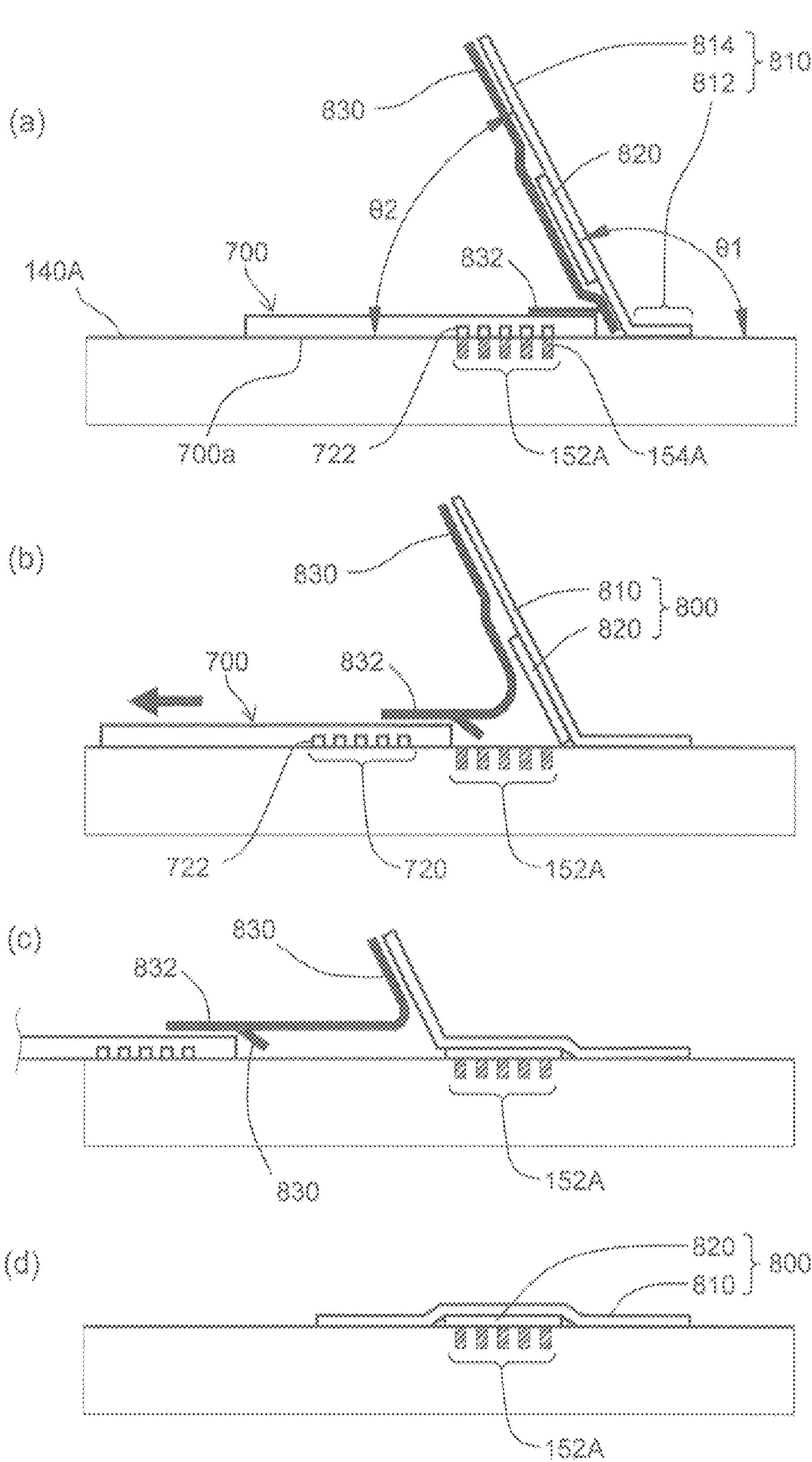
FIG. 24(*a*)-(*d*) are schematic views explaining the principle of positioning (alignment) in the second embodiment of the present invention.

In the second embodiment, as shown in FIG. 24, the patch is located at a given distance in the lateral direction from the porating area, the adhesive sheet is bent at an inner angle θ1, and the second part thereof is maintained at an angle θ2 with the objective-surface (θ1+θ2=180 degrees).

The first and the second embodiments have an intervening release liner as a common special feature. The intervening release liner covers a part (second part) of the adhesive surface of the adhesive sheet and the reservoir, and is fixed to the porator (or porator tab) via attaching feature.

Due to such characteristic, when a user forms micropores in skin by the porator, the other part (first part) of the adhesive sheet adheres to the skin surface of the subject. After formation of micropores, when the user slides (not lifts) the porator along the skin surface, the movement thereof causes the intervening release liner to be peeled from the patch, the reservoir to alignedly cover the porated area, and the adhesive surface of the second part to adhere to the skin surface, whereby adhesion of the patch to the porated area is completed.

As mentioned above, the present invention can minimize and simplify the number of user steps involved in applying the patch while enhancing the repeatability, accuracy and understanding of the steps by users. The present invention also enables adhesion of the patch to the porated area immediately after porating.

The First Embodiment

The first embodiment is explained in detail in the following by referring to a specific preferable example of the constitution.

In the first embodiment, the device at least includes: as shown in FIG. 6 (*a*), a porator having a porator tab (as the patch application support) 420; and a patch 300. In FIG. 6, a porator backing (porator body) is not shown, and only a porator tab is partially shown.

Porator tab 420 is a band-shaped plate in the state of a cantilever with one end (left end of figure) thereof fixed to the porator backing (not shown), and has an objective-surface 420*a* facing outside to be able to contact skin surface 140A of a subject when in use and back-surface 420*b* which is the surface of the opposite side.

As shown in FIG. 6, (c), one or more porating elements 442 are in a porating area in the objective-surface of free end portion (right end of figure) of the porator tab 420. The porating element 442 generates, upon supply of energy, heat at a temperature at which micropores 154A are formed in the surface layer, e.g. stratum corneum, of the skin of a living organism. In the figure, a plurality of porating elements, filaments, form a filament array 444. The porated area is a region defined by a line enveloping one or more porating elements.

The patch 300 comprises at least an adhesive sheet 310 and a reservoir 320 placed in the center of the adhesive surface 310*a*. The reservoir 320 releasably contains a permeant to be delivered through the micropores.

As shown in FIG. 6, (a), the patch 300 is placed on a back-surface 420*b* of porator tab 420, and the reservoir 320 is placed on the back at a position corresponding to the porating area. The adhesive surface 310*a* of the adhesive sheet faces the outside (subject side). An intervening release liner 330 is positioned between the patch 300 and the porator tab 420. The intervening release liner 330 is fixed to the back-surface 420*b* of the porator tab 420.

The adhesive sheet 310 has, as shown in FIG. 7, a first part 312 protruding from the free end and from both longitudinal side edges of the porator tab 420, so that it can adhere to the skin surface 140A of the subject when in use. In FIG. 6 (*a*), the first part 312 protrudes not only from the free end of the porator tab 420 toward right but also to this side and the back side perpendicular to the paper face of the figure. As shown in FIG. 7, therefore, the first part 312 of the adhesive sheet 310 has a U-shape.

The adhesive surface of the remaining second part 314 not protruding from the porator tab and reservoir 320 are covered by an intervening release liner 330. As in FIG. 6 (*a*), the intervening release liner 330 gets away from the patch at a position corresponding to the free end of the porator tab, and turns over, preferably curls around, and is fixed to the back-surface 420*b* of the porator tab 420, via attaching feature (end part) 334.

Due to the above-mentioned constitution, the first part 312 of the adhesive sheet 312 adheres to the skin surface 140A of a subject when in use (particularly when porator is closely adhered to skin surface for poration). As in FIG. 6 (*a*), porating element 442 forms micropores 154A. The region defined by micropores 154A is porated area 152A.

With the first part 312 of the adhesive sheet 310 adhering to the skin surface 140A of the subject, as in FIG. 6, (b)-(e), the porator tab 420 can slide along the skin surface, together with the intervening release liner 330 while peeling off the intervening release liner 330 from the patch 300, and escapes to the outside of the covering area of the adhesive sheet 310 (to left direction of figure). As a result of sliding, as in FIG. 6 (*e*), the reservoir 320 covers the porated area and the adhesive surface of the second part adheres to the skin surface.

As mentioned above, in the device of the present invention, the reservoir of the patch is aligned to be overlapped on the porating area in the assembly stage. During poration, the adhesive sheet 310 fixes the reservoir on the back-surface side 420*b* of the porator tab 420 such that the reservoir 320 is aligned over the filament array 442. However, since the intervening release liner 330 interlays between the porator tab 420 and the adhesive sheet 310, the porator tab 420 can get out, together with the intervening release liner 334, from under the patch 300 adhered to the skin surface 140.

Due to the characteristics, the reservoir 320 can be preferably adhered to the porated area by an extremely simple operation (i.e., by pushing perpendicularly to the skin surface and laterally sliding same along the skin surface);

immediately after porating (without lapse of time);

without exposure of the reservoir to the outside air for a long time;

without touching the adhesive surface or reservoir with finger; and without deviating from the porated area.

Reusable Applicator

As shown in FIG. 8, in a preferable embodiment, the device comprises an applicator 210 as a reusable main body. The porator and the patch form a disposable porator-patch assembly 400, and the porator-patch assembly 400 are replaceably attachable on the applicator 210. In FIG. 8, the porator-patch assembly 400 has a spatula 450. FIG. 8 (*b*) shows the whole device 220, applicator 210 coupled with a porator-patch assembly 400.

The applicator 210 has at least an energy source (not shown) to supply energy to a porating element 442 of the porator. Also, the applicator 210 may contain control electronics (control circuit) and user interface of the system, as well as power electronics (power supply) and pump necessary to achieve a vacuum on the skin and power the porating elements.

Porator-Patch Assembly

Figure 9:
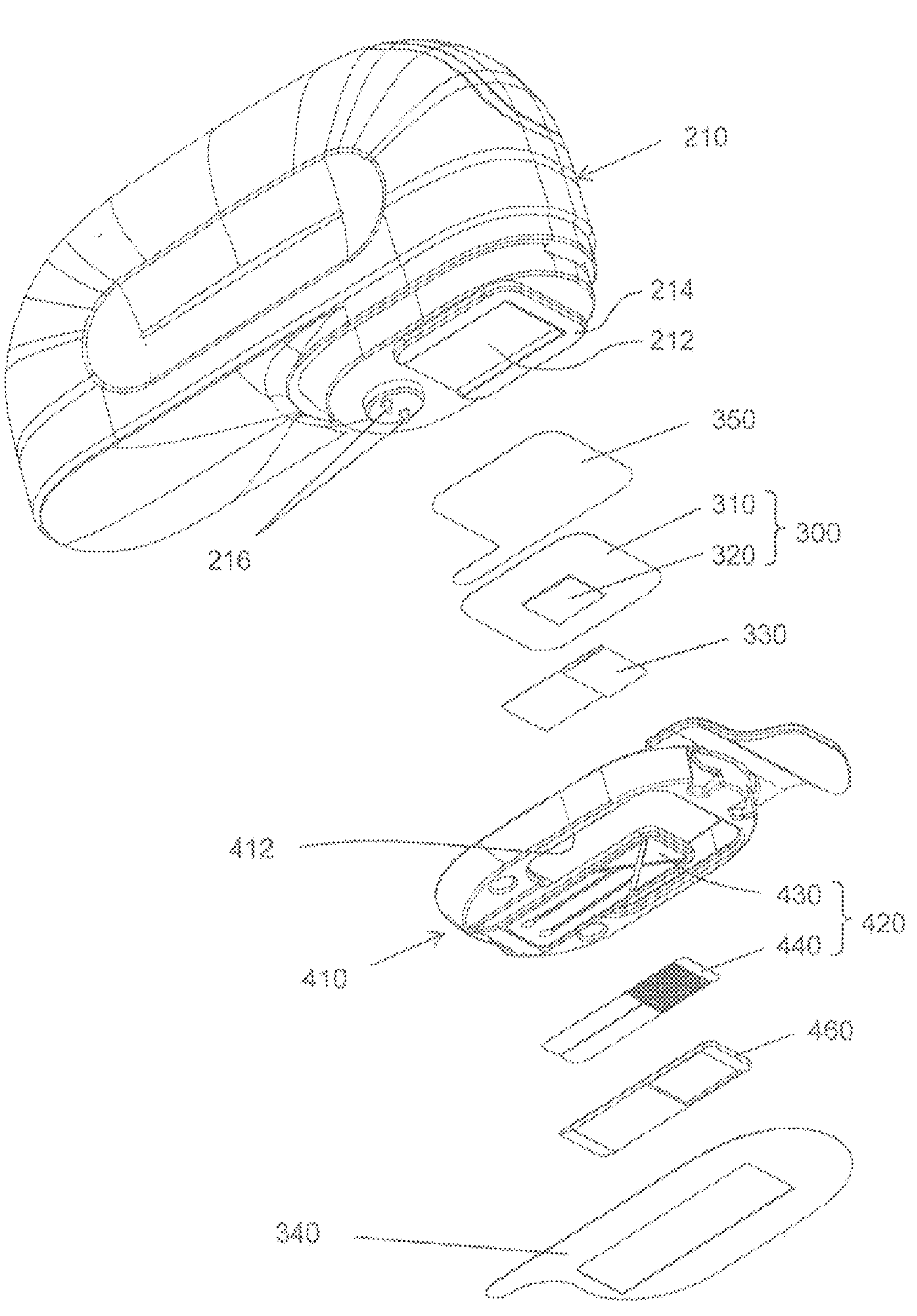
FIG. 9 is an exploded schematic view of the porator-patch assembly of the device shown in FIG. 8, wherein the device is viewed from obliquely below.

In the first embodiment, a porator and a patch are preferably configured as a disposable and replaceable single porator-patch assembly. As shown in FIG. 9, the porator-patch assembly is preferably composed of sub-components comprising:

a porator sub-assembly (porator backing (porator body) 410 with supporting tab 430 and opening 412, a filament array 440, and a porator cover 460); and a patch sub-assembly (patch 300 (comprising an adhesive sheet 310 and a reservoir 320), a bottom release liner 340, a casting sheet 350, and an intervening release liner 330).

Preferably, as shown in FIG. 9, the porator tab 420 has a multilayer structure which is constituted of the band-shaped supporting tab 430, the filament array 440, and the porator cover 460. The filament array 440 may comprise a substrate. One end of the supporting tab 430 is fixed to the porator backing 410, and the supporting tab 430 protrudes as a cantilever beneath an opening 412 of the porator backing 410. The filament array 440 is sandwiched between the supporting tab 430 and the porator cover 460.

The active area 444 (FIG. 12) of the filament array 440 composed of one or more porating elements, filaments, preferably many porating elements, is formed on the objective-surface of the filament array 440 and exposed to the skin surface to be porated, through a window in the porator cover 460. Porating elements, filaments, generate heat on energy supplied from the applicator.

The filament array 440, the porator backing 410, and the porator cover 460 are a sub-assembly assembled separately. The patch 300 is held in shape by the casting sheet 350 on the back-surface (non-adhesive side) and protected on the adhesive side by the combination of the bottom release liner 340 and the intervening release liner 330. The bottom release liner 340 and the intervening release liner 330 are designed so that they jointly cover the adhesive area of the drug patch, without overlapping each other.

The intervening release liner 330 also protects the reservoir.

The porator sub-assembly (410+440+460) is attached to the patch sub-assembly (300+350) via the intervening release liner 330.

Filament Array (as the Array of Porating Elements)

The porating element 442 is constituted to generate heat on supply of energy such as light (e.g., laser beam), sound (e.g., ultrasonication), electric current and the like.

In a preferable embodiment, of this invention, like FIG. 8, the porating element 442 generates heat on supply of electrical energy. It is electrically resistive and is called filament. While the number of the filaments is not limited, for example, 25-500 per square centimeter is preferable. The filaments are configured, for example, as a matrix and constitute the active area 444. Filaments 442 configured in certain shape of the active area 444 are supplied with energy via electrical contacts 446 (FIG. 15), and together constitute filament array (as the array of porating elements) 440.

As for an opening area of one micropore, a center distance between adjacent micropores, and shape and size of the porating area, the prior art may be referred to. The opening area of one micropore is about 0.008 mm2-0.1 mm2. The center distance is about 0.15 mm-3 mm. The preferable shape of the porating area is square, rectangle or circular, but it is not limited. When it is a square, the length of one side thereof is about 3 mm-40 mm, and rectangle and circular shape may have almost the same area as a square.

The porating area (filament array active area 444) is reversely transferred as a porated area on the skin surface.

As for the filaments and the structure of the filament array, energy supply method, temperature control method, and porating method, the prior art such as PCT WO 2008-091878 and the like can be referred to.

Patch: Reservoir

The size of a reservoir 320 can be varied from smaller to larger than the porated area. However, the size of a reservoir 320 is preferably close to the porated area due to maximize a performance and avoid unnecessary poration to a subject. More preferably, the size of a reservoir is not less than that of the porated area according to aligning performance of the system, so that the reservoir can completely cover the porated area.

The device of the present invention has aligning performance with extremely high accuracy. Therefore, the size of the reservoir in the present invention can be close to that of the porated area. For example, when the porated area is a square having one side length of 5 mm-30 mm, the reservoir may be a square having one side length longer than that of the porated area by 0.1 mm-5.0 mm. The same applies even when the porated area has a different shape.

As for the material of the reservoir, the prior art can be referred to and, for example, the reservoir 320 contains at least one or more permeants that are held in a matrix, but not limited. The matrix may be a dried layer, a solid, a semi-solid, a gel, a cream, a liquid, an adhesive or other forms. The supportive materials such as a film, a sponge, a woven, a non-woven, a foam, a membrane, a gauge, a non-porous or a porous materials, may be used.

The permeant releasably contained in the reservoir may be made of any substance utilizable for transdermal or topical delivery, including active agents such as drugs or cosmetics, flux enhancer compounds, osmotic agents, pH control agents or other material. The other aspect of permeant is a hygroscopic nature to control an amount and flux of body fluid through micropores from the living body that is related to a delivery and a monitoring.

The active agents can be a small molecule agent and a macromolecular agent. The macromolecular agents can also be peptides, polypeptides, proteins, anti-bodies, oligonucleotide, polysaccharides or other macromolecules known to be difficult to convey across the skin with existing conventional techniques.

As for the permeant, for example, the prior art can be referred to such as WO 2006-138658, WO 2008-091878, and the like.

The reservoir may be used to absorb a substance that flows out from the living body to the outside through a micropore. In this case, the device of the present invention functions as a transdermal monitoring system.

Patch: Adhesive Sheet

As the material of the adhesive sheet can be used acrylic, silicone, rubber-based adhesives that are coated on the material such as a flexible film, woven, non-woven or foam. Conventionally-known materials can be used, such as polyurethane tape (ex. 3M™ 9832F, 9836, 9833, 9834), polyethylene tape (ex. 3M™ 1503, 1523, 9830, 1525L, 9865, 1526, 9865A, 1522, 1526 and 1521, Avery MED5021, MED1827, MED5020, MED5030), EVA tape (ex. 3M™ 1527ENP, 1527LX and 1527), EVA/polyethylene tape (ex. 3M™ 9835), non-woven tape (ex. 3M™ 9916, 1533L and 9907W, MBK 2501SC, Avery MED5750A), woven tape (ex. 3M™ 1538L, MBK 2503SC), foam tape (3M™ 1772, 1773 and 1774, Avery MED5641), but not limited.

The outer shape of the adhesive sheet may be any as long as it can fix the reservoir to the skin surface, for example, square or rectangle having one side length of about 10 mm-50 mm, or a circular shape having a diameter of about 10 mm-60 mm.

Bottom Release Liner

Figure 10:
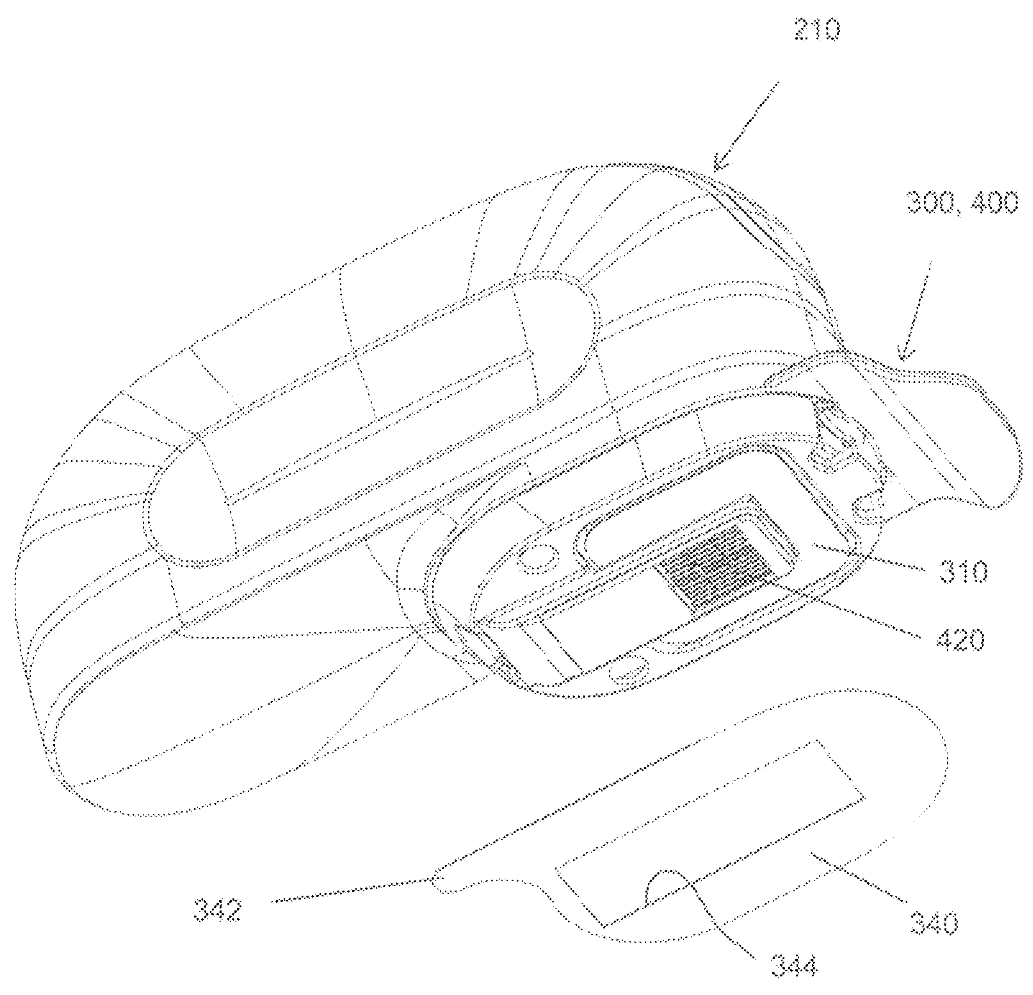
FIG. 10 is a perspective view showing the device in FIG. 8 (*b*) wherein a bottom release liner is peeled off from the porator-patch assembly, and the device is viewed from obliquely below.

As shown in FIG. 10, the tab feature 342 of the bottom release liner 340 allows the user to peal the bottom release liner 340 off, while the cut-out feature 344 allows the bottom release liner 340 to rest flat on the patch 300 by going around the porator tab 420 of the Porator.

As for the material, thickness, and release treatment of the bottom release liner, conventionally-known release liners can be referred to. Preferable examples of the material include, but are not limited to, a fluoropolymer-coated and silicone-coated films (ex. polyester, polyethylene, and polypropylene) or papers. The thickness of the bottom release liner is preferably, for example, about 20 μm-200 μm.

In a preferable embodiment, as shown in FIG. 7, the adhesive area of the adhesive sheet 310 is square path around the reservoir 320. The adhesive area is divided in the U-shaped first adhesive area (the first part 312) and the straight band-shaped second adhesive area (the second part 314).

The bottom release liner 340 covers the U-shaped first adhesive area, while the intervening release liner 330 covers the straight band-shaped second adhesive area.

Casting Sheet

Figure 11:
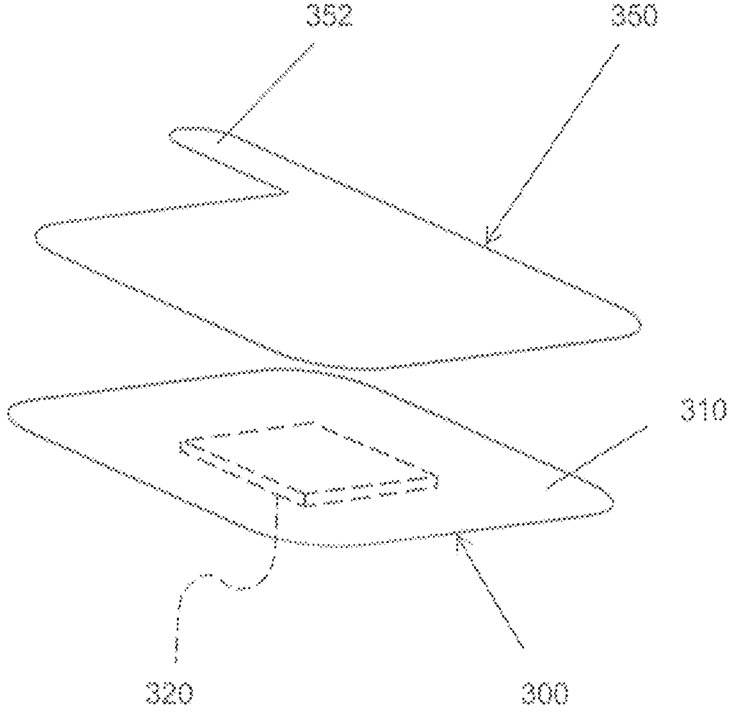
FIG. 11 is a perspective view showing an example of a casting sheet applied to the patch in the present invention.

As shown in FIG. 11, the casting sheet 350 is a stiffer plastic than the adhesive sheet 310 of the patch 300, which is thin and flexible to conform to the skin. The casting sheet 350 maintains the patch's shape while it is not adhere to the skin, and is peeled off by lifting the casting sheet tab 352 after porating and removing the device from the skin.

The casting sheet could be removed from the porator-patch assembly 400 altogether if it was decided that the patch adhesive could be replaced by a stiffer version. This would also remove step, which would also make the overall process simpler and more intuitive.

It must be noted that the drug delivery is still achieved successfully if the casting sheet is not removed by the user.

Porator Tab Geometry and the Applicator Interface

Figure 12:
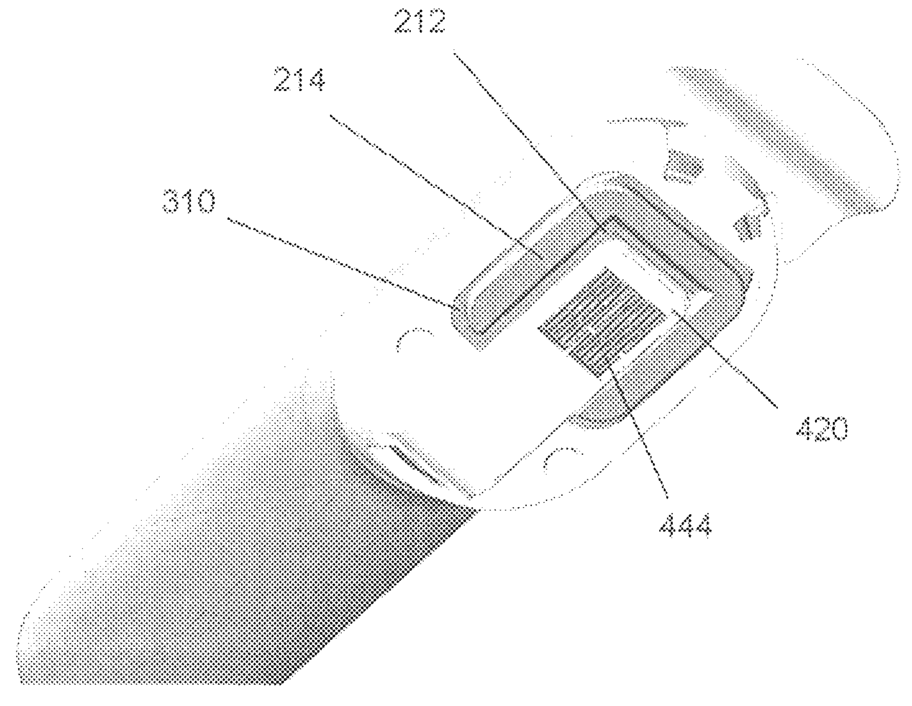
FIG. 12 is a perspective view of the device shown in FIG. 8 (*b*), wherein the porator-patch assembly is viewed from obliquely below, and the features of a porator tab and the periphery thereof are partially enlarged.

As shown in FIG. 8 and FIG. 12, when the porator-patch assembly 400 is clipped into place, the porator tab 420 is centered over a recess feature 212 and inside a protrusion feature 214 of the applicator interface.

Figure 13:
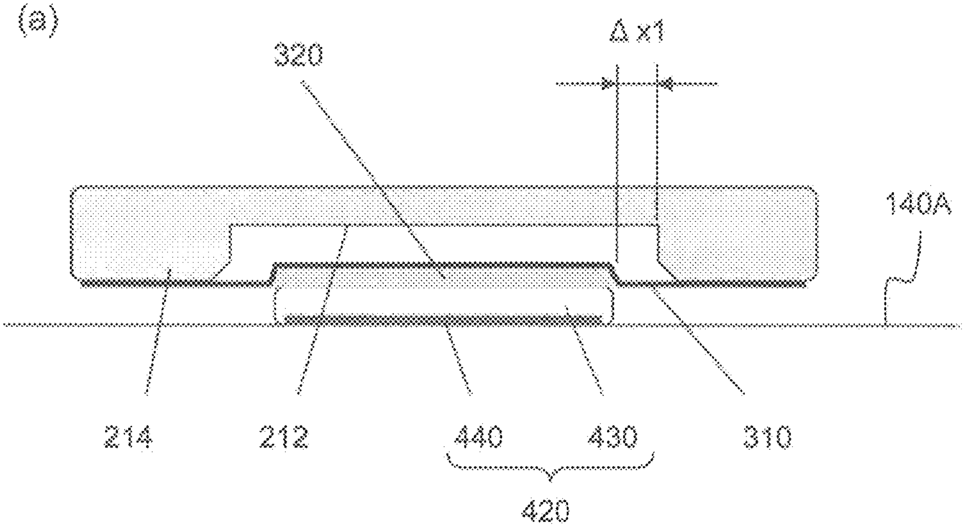
FIG. 13(*a*)-(*b*) are cross-sectional views showing an elastic action of the porator tab and the patch in the porator-patch assembly shown in FIG. 12.
Figure 13:
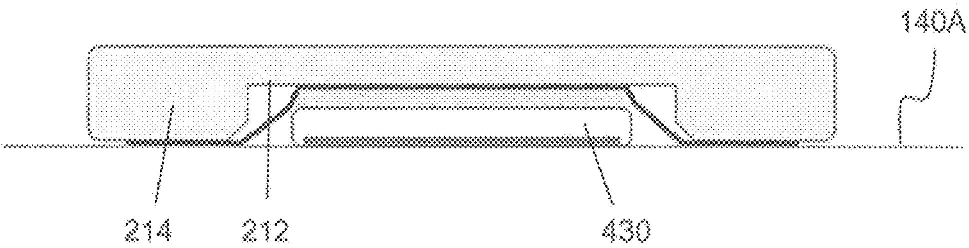

As shown in FIG. 9, the protrusion feature 214 passes through the opening 412 of porator backing and is positioned near the porator tab, as shown in FIG. 13, (a).

The porator tab 420 is thin and designed to flex when pressure is applied to the active area (in a meandering pattern) 444 of the filament array 440. [0044]

As shown in FIG. 13, the relative position of the porator tab 420 and the interface (the recess feature 212 and the protrusion feature 214) enables two functions.

The first is that the recess feature 212 allows the porator tab 430 to flex when the user applies pressure with the applicator on the skin. This ensures optimal contact of the filament array active area onto the skin and enhances the formation of a vacuum (described later).

The second is that when the porator tab 430 flexes, the U-shaped surface of the protrusion feature 214 sandwiches the U-shaped first adhesive area (the first part 312) between itself and the skin, ensuring proper adhesion. The gap xl between the U-shaped interface (the protrusion feature) 214 and the porator tab 420 allows the U-shaped first adhesive area to deform around the porator tab 420 without pinching it. The gap xl is preferably, for example, 0.1 mm-2 mm.

The relative thickness of the porator tab 420 and the width of the U-shaped interface 214 is such that enough of the U-shaped first adhesive area adheres to the skin before poration to ensure stability of the patch 300.

The inner chamfered edge of the U-shaped interface (the protrusion feature) 214 ensures that the interface will not snag onto the reservoir 320 when the applicator is pulled and slid away.

Alignment Over Porated Area

Figure 14:
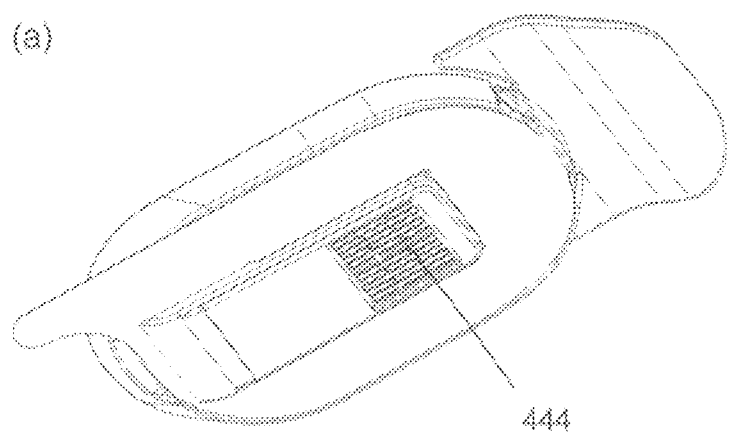
FIG. 14 is a schematic view showing the positional relationship between a porator tab and a reservoir of patch in the porator-patch assembly shown in FIG. 12.
Figure 14:
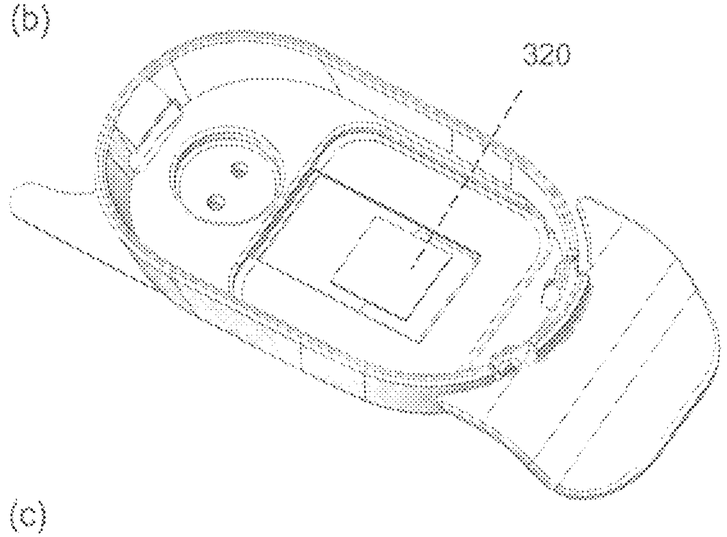
Figure 14:
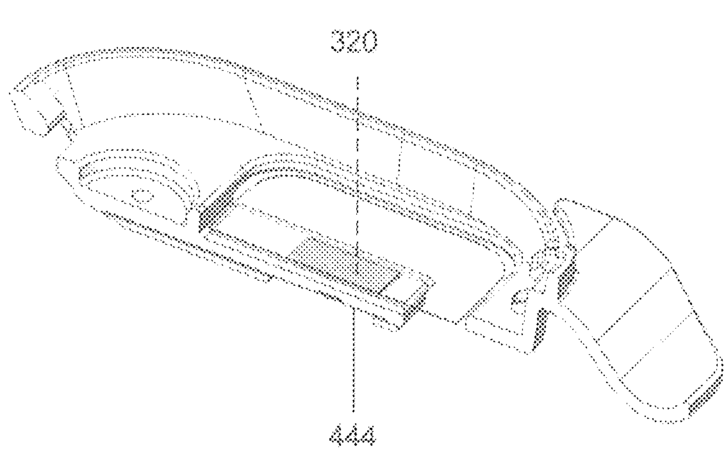

As shown in FIG. 14, the crucial aspect of this invention is that it ensures that the reservoir 320 is directly placed over a back-side of the active area 444 of the filament array 440.

When the U-shaped first adhesive area has adhered to the skin, this setup guaranties that the reservoir 320 will be precisely applied to the porated area 152A (FIG. 6) of the skin.

Electrical Contacts and Vacuum Path

Figure 15:
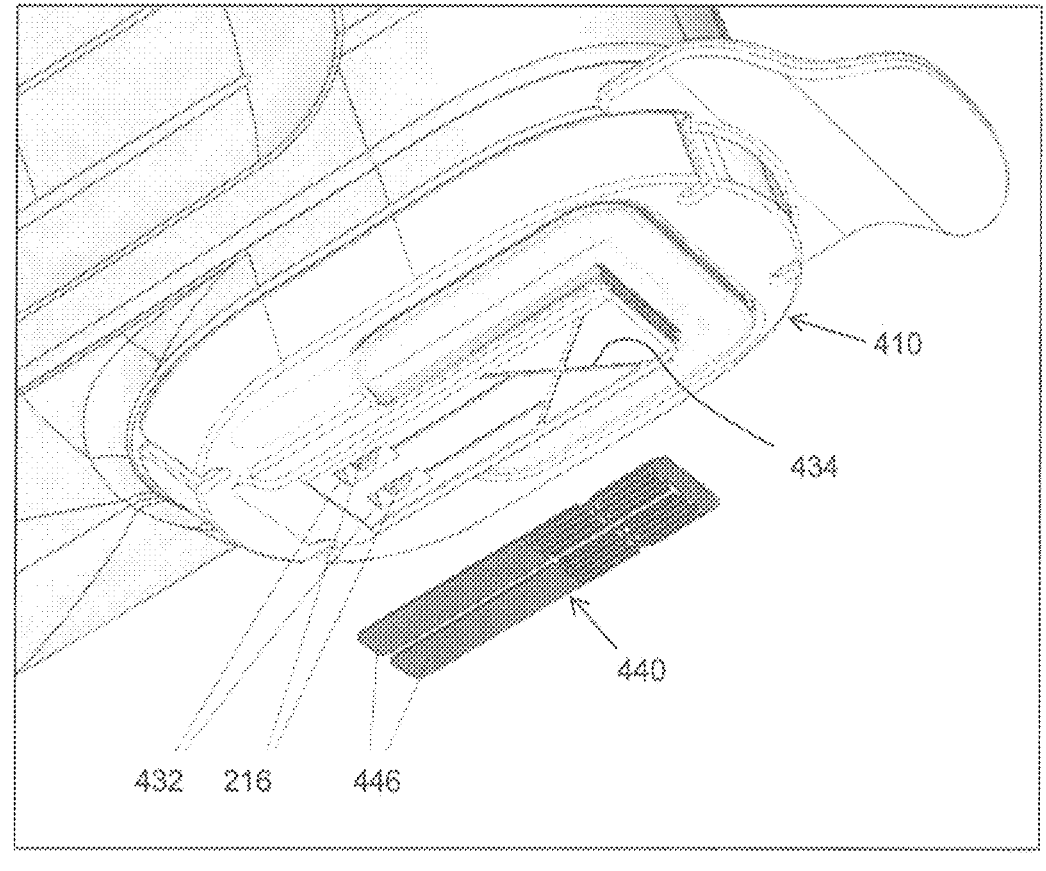
FIG. 15 is an exploded schematic view showing a specific constitution example of the porator tab in the porator-patch assembly shown in FIG. 12, wherein the porator-patch assembly is viewed from obliquely below.

As shown in FIG. 15, the porator backing 410 (particularly, the base end (root) of supporting tab 430) features one or more pass-through (two pass-throughs in the figure) 432 that allows the electrical leads 216 of the applicator 210 to contact the leads 446 of the filament array 440. This allows current from the applicator 210 to power the filaments within active are 444.

The filament array leads 446 close off the vacuum channels 434, creating a closed path from the pass-throughs 432 to the filament array active area 444. This allows the applicator to apply a vacuum to the porated area on the skin while porating.

Intervening Release Liner

As shown in FIG. 6, the intervening release liner 330 protects the reservoir 320 as well as the straight band-shaped second adhesive area (the second part 314). The intervening release liner 330 turns over, preferably curls around (feature 332) and is affixed to the porator tab (supporting tab 430) via end part 334.

It is preferably that feature 332 is a curl and not a fold, because this allows a smooth rolling when the Applicator is pulled and slid away. A fold offers an initial resistance to "rolling" away, which is not conducive to a proper and intuitive removal.

Figure 17:
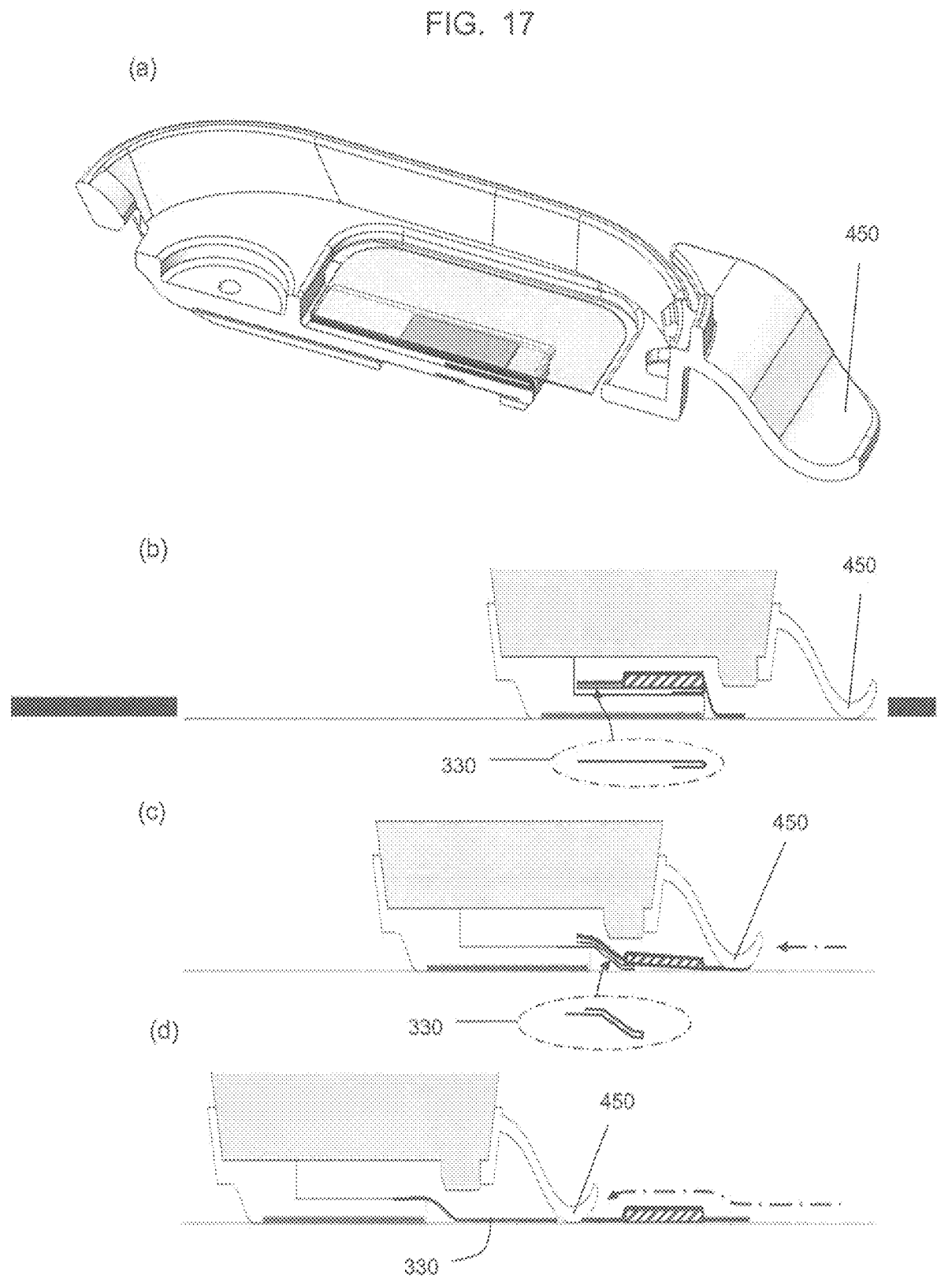

As shown above in FIG. 6, (b)-(e) and FIG. 17, (b)-(d) the intervening release liner 330 remains attached to the porator tab 420 as it is pulled away, progressively exposing the reservoir 320 to the porated area of the skin, and the adhesive second (second part 314) to the periphery of the porated area.

As for the material, thickness, and release treatment of the intervening release liner, conventionally-known release liners can be referred to. Preferable examples of the material include, but are not limited to, a fluoropolymer-coated and silicone-coated films (ex. polyester film, polyethylene film, and polypropylene, or papers). The thickness is preferably, for example, about 20 μm-250 μm.

The length of the intervening release liner is, between one length and two lengths of the porator tab 430, and is not interfering with the spatula contact front 452, explained later. Width must be capable of covering the reservoir and porator tab 430 width, and minimally overlap with the cut-out feature 344 of the bottom release liner 340.

Spatula

In a preferable embodiment of the present invention, the principle of the action is schematically shown in FIG. 16, wherein the spatula 450 is imparted to the porator backing or the applicator. In the embodiments shown in FIG. 8-FIG. 19, a plate spatula 450 is integrally formed on the porator backing.

The broken lines in FIG. 16 suggest that spatula 450 is fixed on the porator backing (or the applicator). The spatula extends from the porator backing to a contacting area laterally away from the porating area (porated area 152A in FIG. 16 (*a*)).

When in use, after porating in FIG. 16 (*a*), as shown in FIG. 16, (b)-(e), the porator tab 420 slides towards its fixed end side along the skin surface, during which the spatula 450 also follows the porator tab 420 to press and smooth the adhesive sheet 310 against the skin surface 140A while sliding on the adhesive sheet 310.

Using the spatula, users can also complete smoothing of the patch after porating by merely sliding the device along the skin surface.

The shape of the spatula is not particularly limited and may be any as long as the above-mentioned action is obtained, and may be a plate or a bulk or a combination thereof. It is preferably an elastic plate having a smooth convex surface, which is formed on its tip on the objective-surface side as a contacting part 452, like the scoop shape shown in FIGS. 8-19, since the material can be saved and the patch can be elasticity smoothed. The width of the spatula (in FIG. 16, the size in the direction perpendicular to the paper surface) is preferably not less than the patch of the adhesive sheet to smooth the whole patch, for example, about 15 mm-40 mm.

In the embodiments of FIGS. 8-19, the spatula is formed from a plastic material integrally with the housing of the porator, and the thickness thereof is, for example, about 1 mm-2 mm.

As shown in FIG. 16 and FIG. 17, (b)-(d), the spatula 450 smooths over the patch 300 as the device (applicator and porator-patch assembly) is pulled and slid away from the porated area.

The contacting part 452 on the spatula tip may be at a position far from the porator or applicator by not less than a particular distance. The position thereof is, as shown in FIG. 16, (e), farther apart from the tip of the fully-developed intervening release liner 330 and does not contact the liner. When the contacting part of the spatula is placed at a position closer than the fully-developed intervening release liner, the spatula presses the intervening release liner 330 from above the adhesive sheet before complete evacuation of the intervening release liner 330 from under the adhesive sheet and prevents preferable sliding and smoothing.

Figure 18:
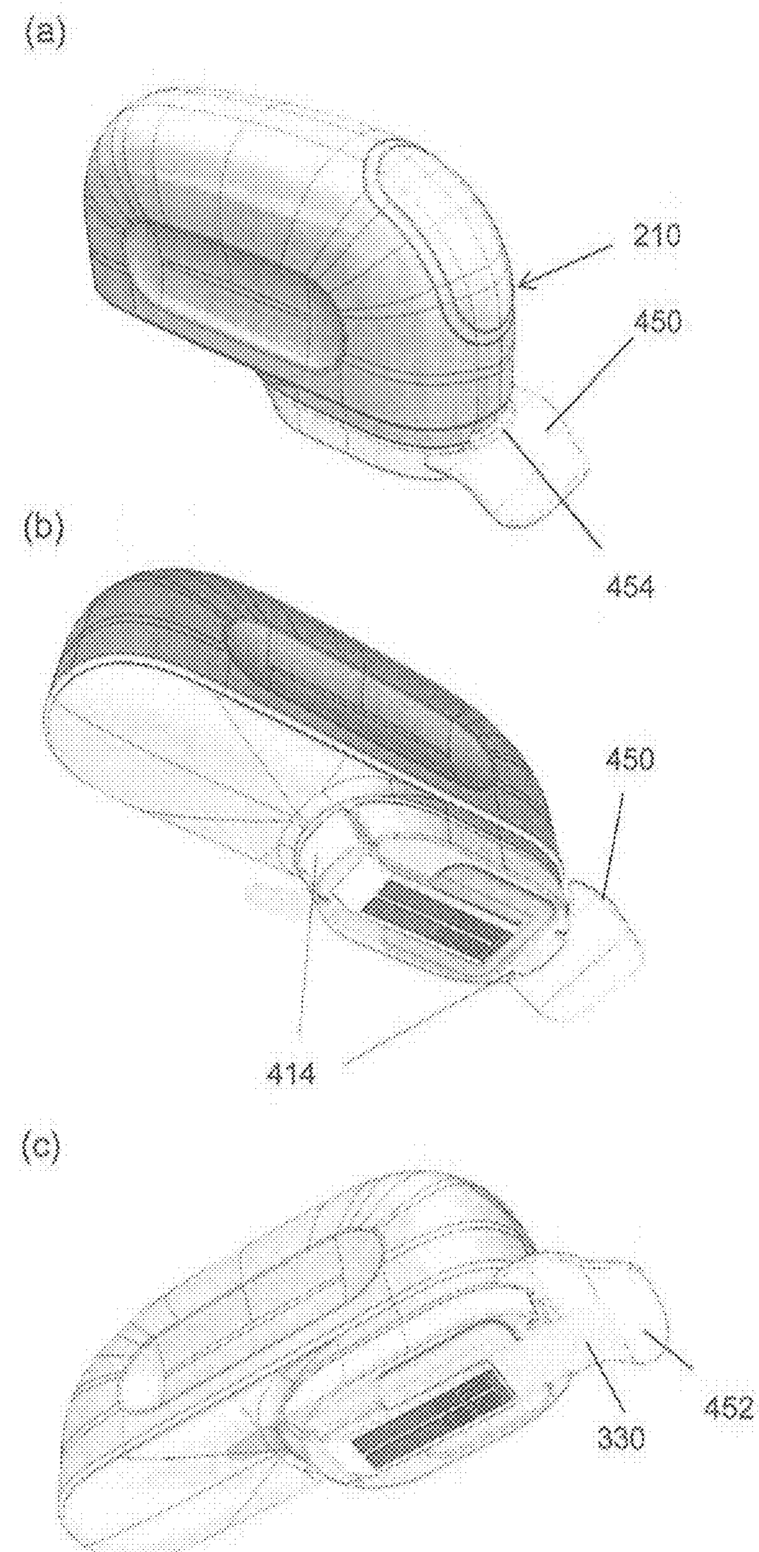
FIG. 18(*a*)-(*c*) are perspective views showing a preferable detailed structure of the porator-patch assembly shown in FIG. 12.

As shown in FIG. 16, (e), and FIG. 18, (c), a contacting part 452 is positioned in such a way that when the intervening release liner 330 is completely uncurled, the contacting part 452 does not pinch the intervening release liner 330 on the skin. If the spatula did pinch the intervening release liner, this would stop the uncurling and prevent the device from sliding away.

Others

As shown in FIG. 18, (a), the stress relief ridge 454 on top of the spatula allows stress to transfer onto the applicator body instead of straining the porator when force is applied to the spatula 450.

As shown in FIG. 18, (b), clips 414 allow the porator-patch assembly 400 to remain attached to the applicator 210.

The spatula 450 also double as a lever (handling tab) that allows the user to un-clip the porator-patch assembly from the applicator by flexing the clips 414 away from the applicator.

Figure 19:
FIG. 19(*a*)-(*c*) show continuous photographs showing the use state of the first embodiment of the device of the present invention.
Figure 19:
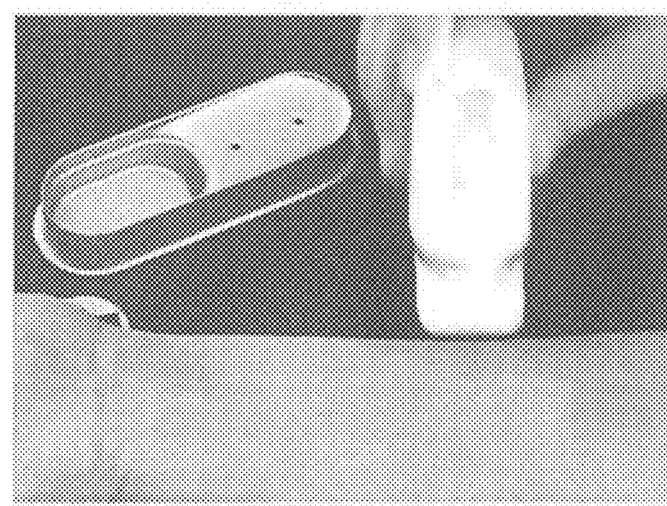
Figure 19:
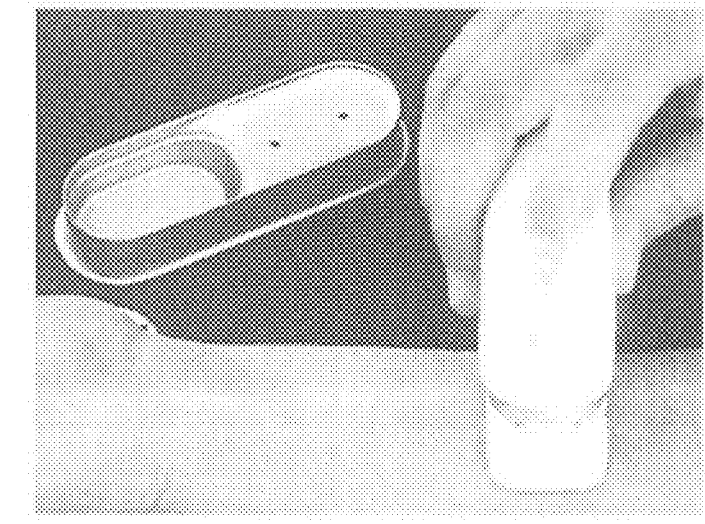
Figure 19:
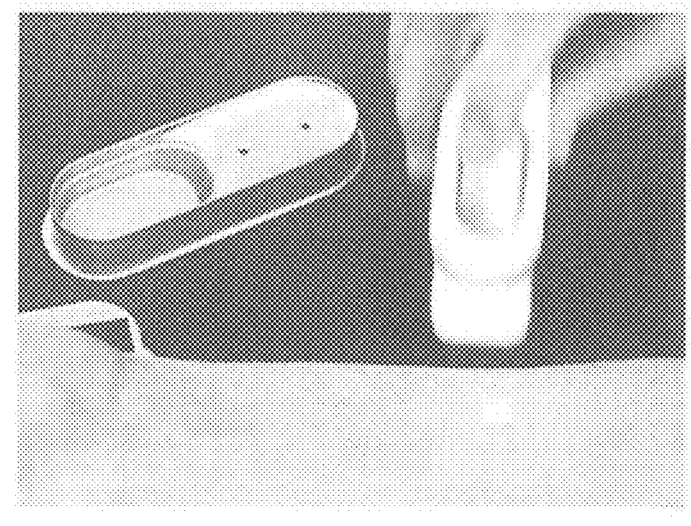

As shown in FIG. 19, according to the first embodiment of the present invention, users press the device against a skin surface (from (a) to (b)) and then, after indication of the lamp, merely slide the device along the skin surface, whereby the porated area and the patch adhered thereon can be obtained.

Roller

As shown in FIG. 20, the device may have a roller 500 instead of the spatula. Each part other than the roller is the same as in the device having the spatula. The roller 500 is placed at a position apart in the lateral direction from the porating area, like the contacting part 452 of the spatula 450 shown in FIG. 18. When FIG. 16 and FIG. 20 are compared, it is clear that the roller 500 is replaced by the spatula.

The broken lines in FIG. 20 suggest that roller 500 is fixed on the applicator (or porator). Roller 500 is placed in a contacting area laterally away from the porating area (porated area 152A in FIG. 20 (*a*)). When in use, after porating in FIG. 20 (*a*), as shown in FIG. 20, (b)-(e), the porator tab 420 slides towards its fixed end side along the skin surface 140A, during which the roller 500 also follows, like the spatula, the porator tab 420 to smooth and press the adhesive sheet 310 against the skin surface 140A while rolling on the adhesive sheet 310.

Using the roller, users can also complete the smoothing of the patch by merely sliding the device along the skin surface after porating.

As compared to the spatula which may simply be a single board, the roller requires many parts. Therefore, the roller is preferably reusably attached to the applicator rather than being disposable.

Figure 21:
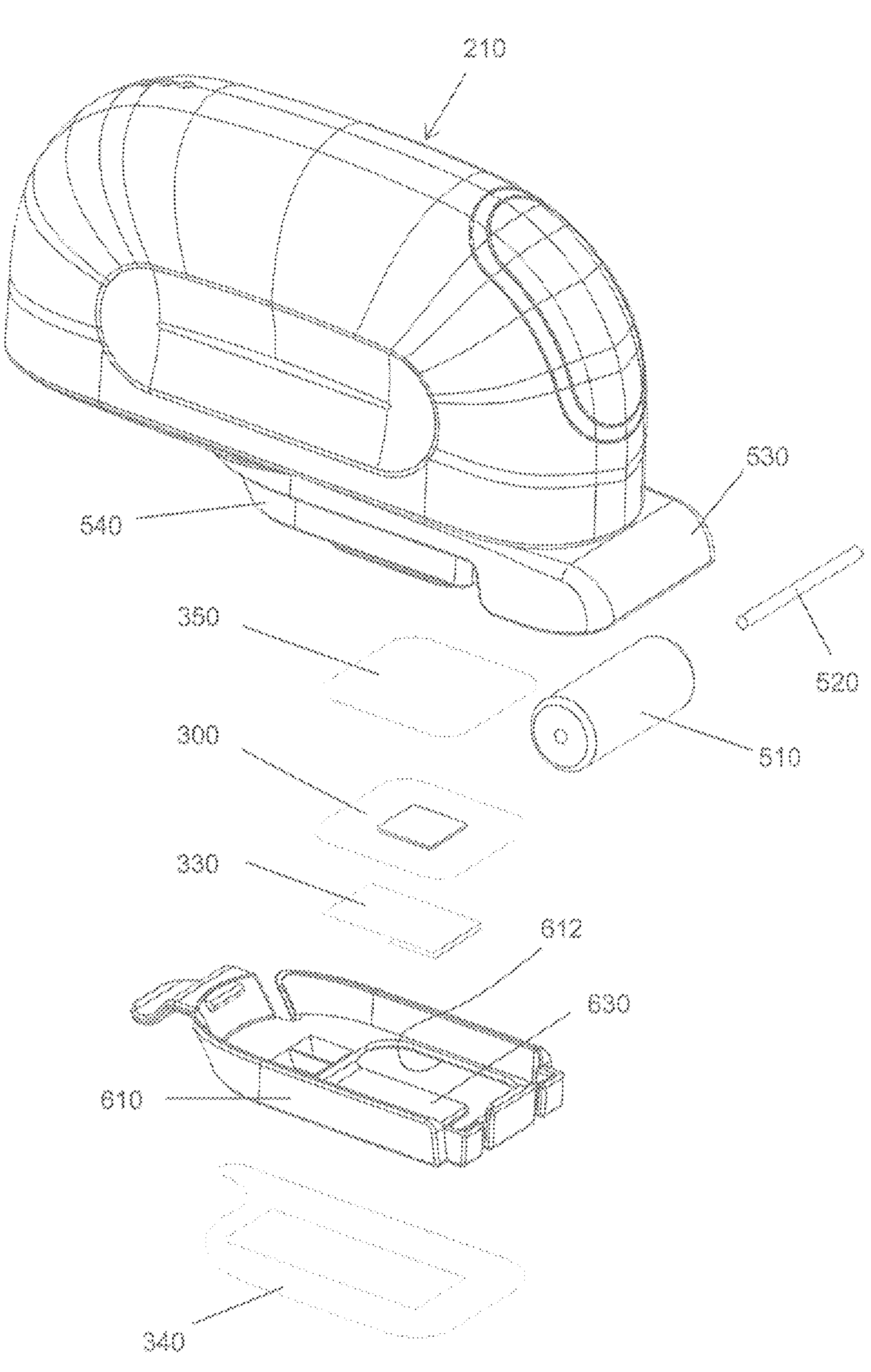
FIG. 21 is an exploded schematic view of the device with a roller shown in FIG. 20.
Figure 22:
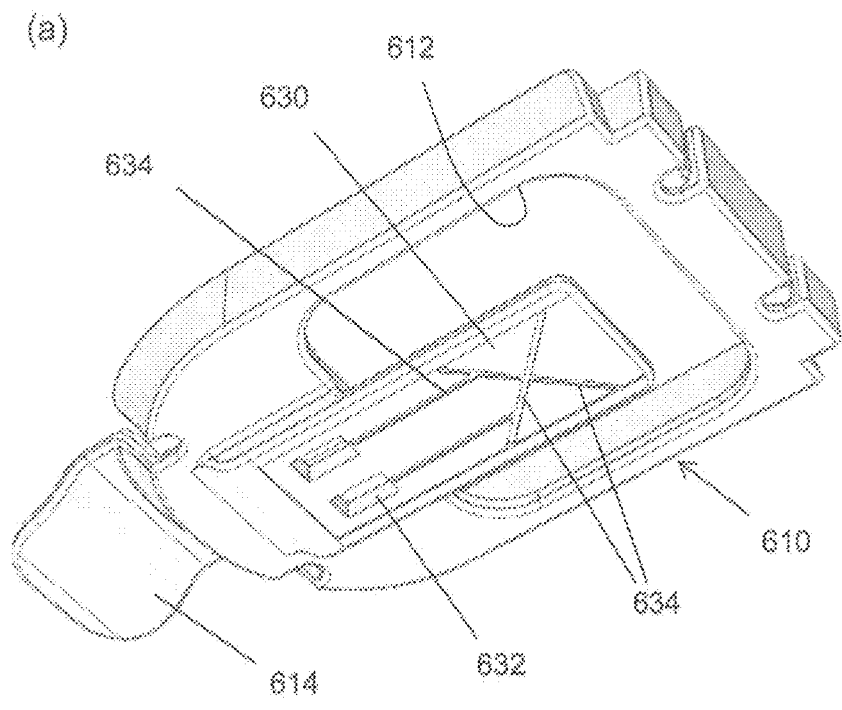
FIG. 22 is a perspective view of the porator backing shown in FIG. 21.
Figure 22:
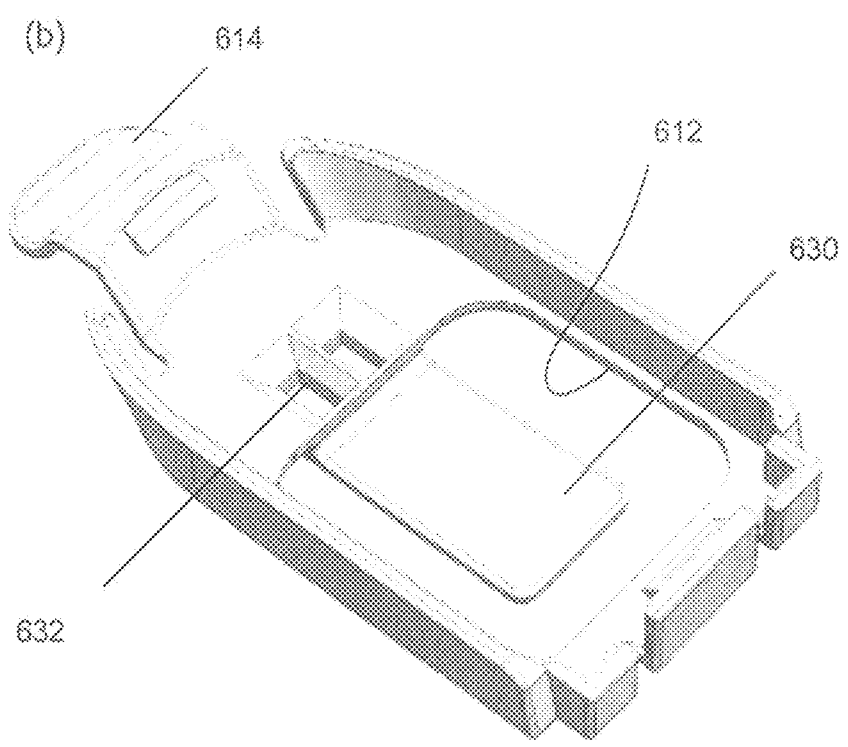

FIG. 21 is an exploded schematic view of a preferable embodiment of the first embodiment having a roller. Similar to the device of FIG. 9 having the spatula, in this embodiment of FIG. 21, the porator and the patch are assembled as one disposable and exchangeable porator-patch assembly also in a device having a roller. As shown in FIG. 21 and FIG. 22, the porator-Patch assembly is preferably composed of sub-components comprising:

porator sub-assembly (porator backing 610 (with supporting tab 630 and opening 612), and porator substrate with filament array (not shown); and patch sub-assembly (patch 300 (comprising adhesive sheet and reservoir), bottom release liner 340, casting sheet 350, and intervening release liner 330).

Each element other than the roller of the sub-assembly is the same as that of a sub-assembly in a device having a spatula, and as explained above.

In the device having the roller, as shown in FIG. 21, a holder 530 for the roller is preferably provided in the applicator 210. In the holder 530, the cylinder 510 and the center shaft 520 are held, whereby the roller is constituted. Like the spatula, the roller is placed in a contacting area laterally away from the porating area. While the diameter of the roll is not limited, about 10 mm-14 mm is preferable.

As shown in FIG. 20 (*e*), and FIG. 23 (b5), the position of the contacting area is farther away from the tip of the fully-developed intervening release liner 330 and does not contact the liner. When the roller is placed at a position closer than the fully-developed intervening release liner, as shown in FIG. 23 (b4), the roller presses the intervening release liner 330 from the top of the adhesive sheet before complete evacuation of the intervening release liner 330 from under the adhesive sheet and prevents preferable rolling and smoothing.

As shown in FIG. 23, (a), the roller (particularly, contacting front 512 of the cylinder) is positioned in such a way that when the intervening release liner 330 is completely uncurled, the roller does not pinch the intervening release liner 330 on the skin. If the roller did pinch the intervening release liner, this would stop the uncurling and prevent the device from sliding away.

As shown in FIG. 22, other than the spatula, the porator backing 610 of the device having the roller may have the same structure as that of the porator backing 410 shown in FIG. 9. In one end, the supporting tab 630 is fixed to a porator backing 610, and the other end protrudes as a cantilever beneath an opening 612 of the porator backing 610. The porator backing 610 (particularly, base of porator tab 630) features two pass-throughs 632 that allows the electrical leads (not shown) of the applicator to contact the filament array leads through the porator substrate. This allows electrical current from the applicator to power the filament array.

The filament array leads close off the porator vacuum channels 634, creating a closed path from the pass-throughs 632 to the filaments of the active area. This allows the applicator to apply a vacuum to the porated area on the skin while porating.

The porator backing 610 is free of the spatula as a handling tab at a front end, but has a roller immobilized on the applicator. Therefore, the porator backing 610 may further have a handling tab 614 at a rear end.

User Steps

The first embodiment of the present invention (having the spatula or the roller) requires fewer steps than the known techniques:

A. Clip on the porator-patch assembly to the applicator,
B. Remove the bottom release liner,
C. Apply the applicator to skin, and wait several seconds (porating),
D. Slide the applicator away (the patch remains on the porated area),
E. Remove the casting sheet (if needed).

By positioning the patch above the porated area and applying it in one sliding motion, the directional slide spatula or the roller removes step responsible for four critical user-related risks.

By automatically removing the intervening release liner that protects the active drug compound, not requiring a folding over step and smoothing the patch in the same motion, the spatula or the roller diminishes overall steps by one third, simplifying the process and making it straightforward.

The spatula or the roller allows for an easy removal of the casting sheet.

The spatula or the roller on the device implies a directionality which leads users to remove the applicator by sliding away. This diminishes misuse.

The Second Embodiment

The second embodiment is explained in detail in the following by referring to specific preferable constitution examples.

In the second embodiment, the device has, as shown in FIG. 24 (*a*), at least a porator 700 and a patch 800. In FIG. 24, only the objective part of the porator 700 is partially shown for explanation. The second embodiment does not need to have a porator tab used in the first embodiment.

The porator 700 has an objective-surface 700*a* facing outside to be able to contact skin surface 140A of a subject when in use. One or more porating elements are formed in the porating area in the objective-surface. The porating element itself, filament, is the same as in the first embodiment. In FIG. 24, like FIG. 6, a plurality of porating elements 722 form a filament array with active area 720. The active area is the region defined by a line enveloping one or more filaments.

Patch 800 has at least an adhesive sheet 810 and a reservoir 820 placed in the approximate center of the adhesive surface. The structure itself of the patch is the same as in the first embodiment, and the reservoir releasably contains a permeant to be delivered through the micropores.

As shown in FIG. 24 (*a*), the adhesive sheet 810 of the patch 800 is bent at an given inner angle 81 (0 degrees<81<180 degrees), with the adhesive surface facing outside. The bending line thereof divides the adhesive sheet 810 into a first part 812 and a remaining second part 814.

The first part 812 of the adhesive sheet 810 is placed in an extended plane of the objective-surface 700*a* so that it can adhere to the skin surface 140A of the subject when in use. The bending line is located on the side closer to the porating area in the outer circumference of the first part 812, and the second part 814 stands up at the inner angle 81, with the adhesive surface facing the porating area.

The reservoir 820 is fixed at a given position on the adhesive surface of the second part 814 of the adhesive sheet

810, such that the reservoir 820 and the porating area about the bending line correspond symmetrically.

The adhesive surface of the second part 814 of the adhesive sheet 810 and the reservoir 820 are covered with an intervening release liner 830. As shown in FIG. 24 (*a*), the intervening release liner 830 is connected to the porator 700 in the vicinity of the bending line.

Due to the above-mentioned constitution, the first part 812 of the adhesive sheet 810 in the porator adheres to the skin surface 140A of the subject when in use (particularly when porator is closely adhered to the skin surface for porating). As in FIG. 24 (*a*), filaments 722 form micropores 154A. The region defined by the micropores 154A is the porated area 152A.

With the first part 812 of the adhesive sheet 810 adhering to the skin surface 140A of the subject, as in FIG. 24 (*b*)-(*d*), the porator 700 is slidable along the skin surface, together with the intervening release liner 830 while peeling off the intervening release liner 830 from the patch 800, to the outside of the area to be covered with the adhesive sheet 810 (slidable to left direction of the figure). As a result of sliding, as in FIG. 24 (*d*), reservoir 820 covers the porated area 152A and the adhesive surface of the second part adheres to the skin surface.

Figure 26:
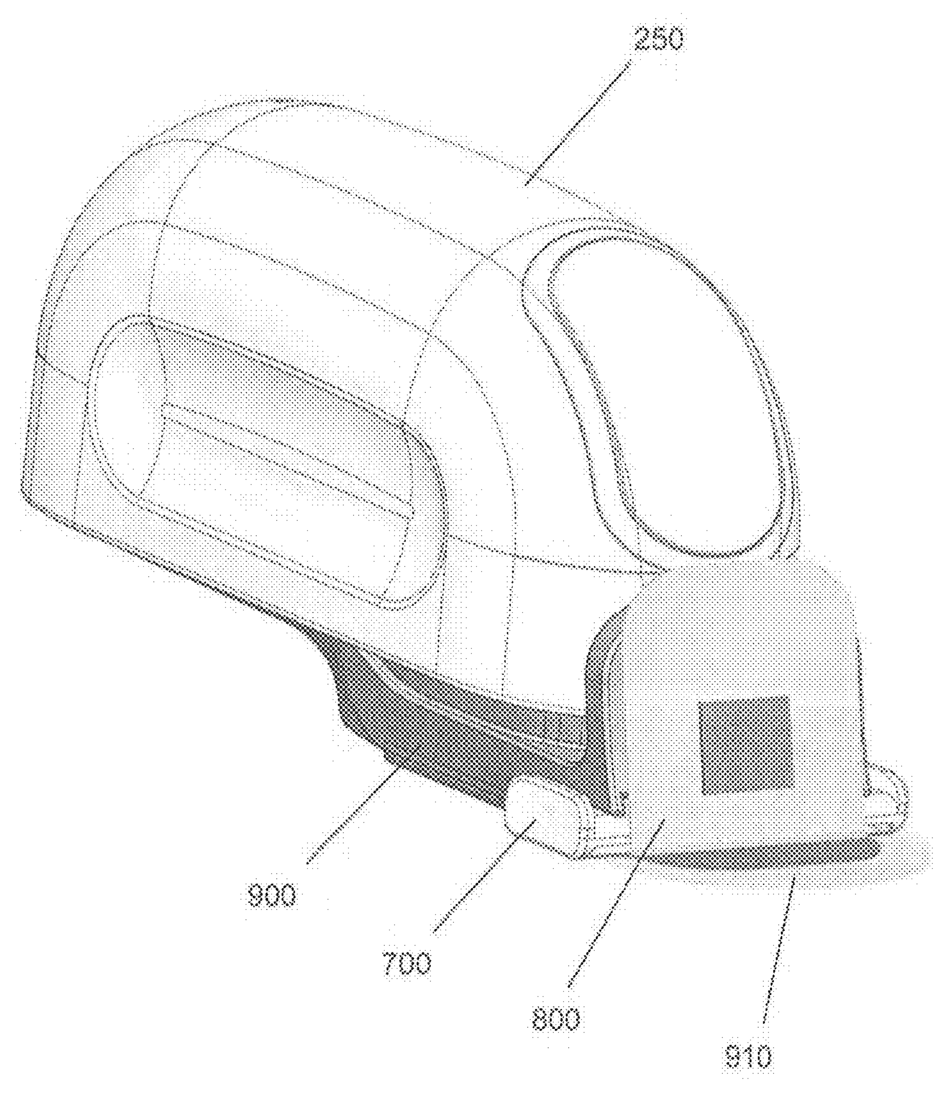
FIG. 26 is a perspective view showing the appearance of Example of the second embodiment of the present invention.

As shown in FIG. 25 and FIG. 26, the second embodiment of the device also has an applicator 250 as a reusable main body as in the first embodiment, and the applicator 250 has at least an energy source for energy supply to the filaments of the porator 700, and the porator 700 and the patch 800 are preferably replaceable in the applicator. In the embodiments of FIG. 25 and FIG. 26, the porator 700 and the patch 800 are attached to and detached from the applicator 250 via an interface 900.

FIG. 25 is an exploded schematic view of a preferable embodiment of the second embodiment. As in the first embodiment, porator and patch are assembled as one disposable and exchangeable porator-patch assembly also in a device having the roller. As shown in FIG. 25, the patch 800 comprises the adhesive sheet 810 and reservoir 820, and further comprises bottom a release liner 840 and a casting sheet 850.

The casting sheet 850 is bent like the adhesive sheet, and the bending line divides the casting sheet 850 into the first part 852 and the remaining second part 854.

The intervening release liner 830 is the same as a release liner, though different in the shape and bending angle, from the intervening release liner in the first two embodiments.

The material and size of each element of the patch are the same as those of each element of the first embodiment, and as explained above.

Also, one or more filaments may be in a filament array. One or more filaments are, as in the previous embodiments, part of a filament array, and the filament array is preferably attached to the porator backing and constitute the porator 700. To show the bottom surface of the porator backing, the filament array is not shown in FIG. 28, FIG. 29.

Also, the applicator may have a vacuum source as in the first two embodiments and the porator may be provided with a path to allow for application of the sucking force of the vacuum from the vacuum source to the skin surface of the subject. These materials, structures and sizes are the same as those of each element of the first embodiment, and as explained above.

The inner angle θ1 of the adhesive sheet 810 of the patch 800 is preferably 30 degrees-150 degrees, more preferably 90 degrees-150 degrees, further more preferably 115 degrees-130 degrees.

While the area ratio of the first part 810 of the adhesive sheet and the remaining second part 814 is not limited, (first part 810: second part 814)=(1:6)-(1:2) is preferable in consideration of the effective size of the reservoir and the size of the adhesive sheet relative thereto.

Intervening Release Liner

As shown in FIG. 24, the intervening release liner 830 protects the reservoir 820 as well as the straight band-shaped second adhesive area (the second part 814). The intervening release liner 830 folds over, and is affixed to the porator 700 via attaching feature 832. The attaching feature may be a part branching out from the intervening release liner 830 or a bent end part of the intervening release liner 830. Unlike in the case of "scoop" and "roller" embodiments where it is preferred the feature 332 (FIG. 6) is a curl and not a fold, in this embodiment that is not necessary. Since the patch adhesive 810 and intervening release liner 830 are already positioned under angle different than 180 degrees, a smooth rolling, without initial resistance, and de-peeling action will be provided when the applicator is pulled and slid away.

As shown above in FIG. 24, (b)-(d) the intervening release liner 830 remains attached to the porator 700 as it is pulled away, progressively exposing the reservoir 820 to the porated area of the skin, and the adhesive second (second part 814) to the periphery of the porated area.

As for the material, thickness, and release treatment of the intervening release liner, conventionally-known release liners can be referred to. Preferable examples of the material include, but are not limited to, silicon coated PET films. The thickness is preferably, for example, about 20 μm-250 μm.

The width of the intervening release liner 830 need to be at least the same as the width of the patch adhesive 810 cover the width of the. The length of the intervening release liner 830 needs to be equal to the length of the patch adhesive 810 plus the length of the feature 830, the part which permanently attach it to the porator 700.

Interface

Figure 27:
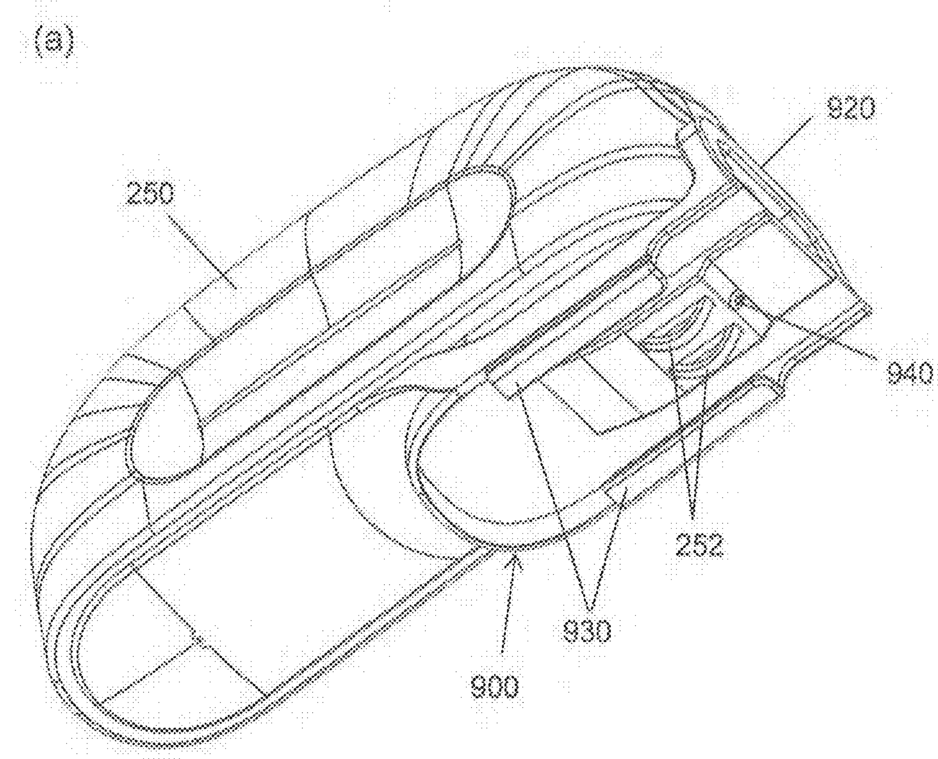
FIG. 27 is a perspective view of the interface in the second embodiment of the device of the present invention.
Figure 27:
Figure 27:
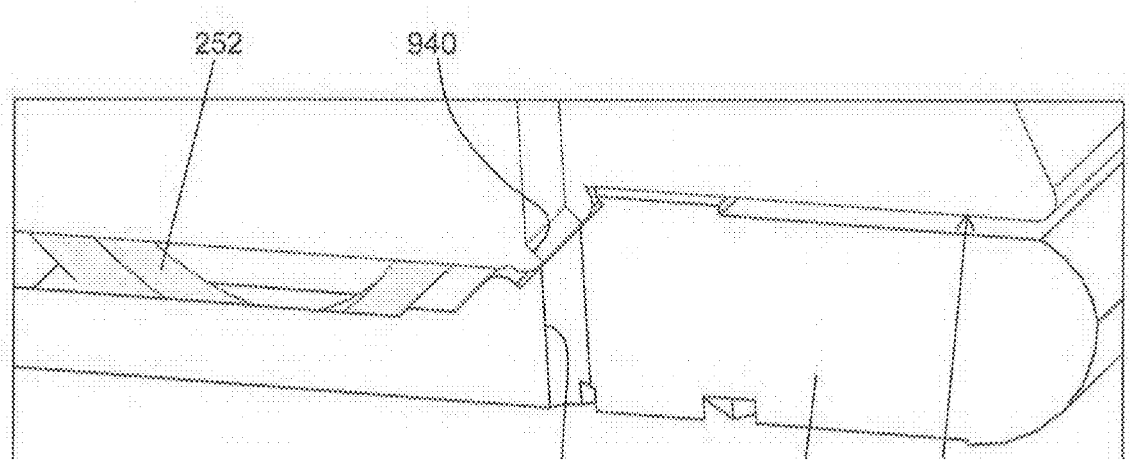
Figure 28:
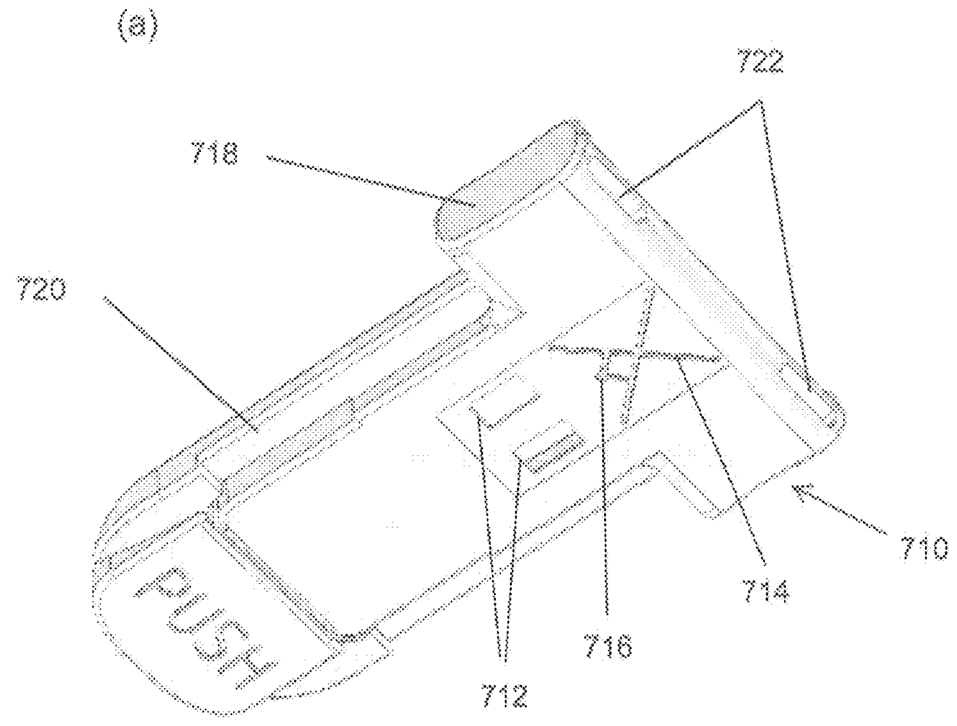
FIG. 28 is a perspective view of the porator backing in the second embodiment of the device of the present invention.
Figure 28:
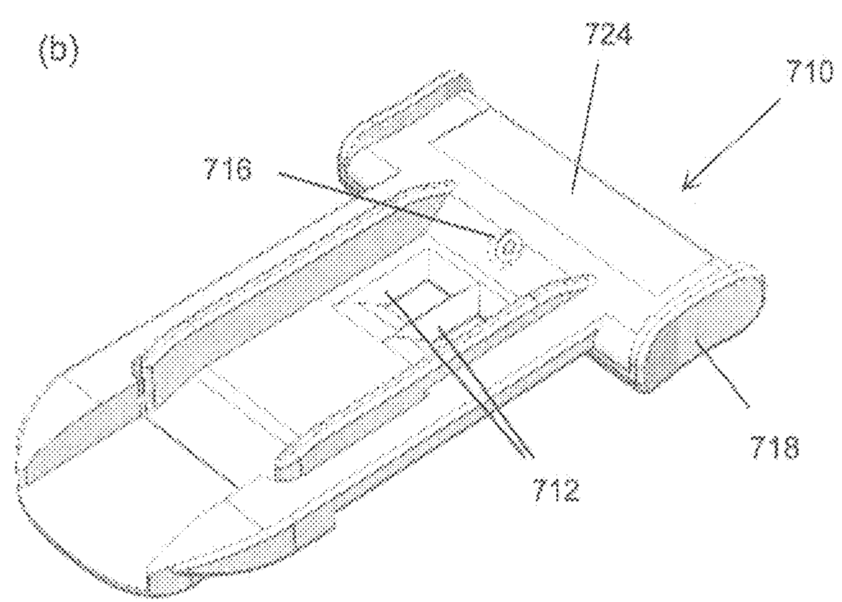

As shown in FIG. 27, in a preferable embodiment, the applicator 250 has, on its bottom surface, an interface 900 for attaching a porator. In the embodiment of FIG. 27, the interface 900 has a pair of claws 930 to hold the porator backing at the both longitudinal side edges thereof. As shown in FIG. 28, flexible clip 720 for elastically engaging the porator backing to the claws 930 is formed around the both longitudinal side edges thereof. The porator is slidably attached into and detached from the claws 930 from the front part of the applicator.

The electrical contacts 252 (protruded from the applicator 250) are arched to allow sliding insertion of the porator, and to allow contact after insertion of the porator.

A vacuum path 940 is open in the inclined (at 45 degrees) surface facing forward. On the other hand, as shown in FIG. 28, (b), a vacuum path (through-hole) 716 is open on the top surface of the porator backing 710 facing backward. As shown in FIG. 27, (b), these paths enable sliding insertion action of the porator to form a vacuum connection.

The patch frame 920 is the integral part of the applicator-porator interface 900. After inserting porator-patch assembly into applicator, it lifts-up unattached part of a patch, providing temporary support for the structure (830+820+814+854) and also defines angle 81.

Porator

As in the embodiment of FIG. 15, the porator 700 in FIG. 28 incorporates the filament array (not shown) having filaments, and porator cover with a window to enable filaments to contact skin and achieve vacuum. Only the porator backing 710 is shown in FIG. 28.

The porator backing 710 features two pass-throughs 712 that allows the electrical contacts 252 of the applicator 250 to contact the array leads of the porator substrate. This allows current from the applicator 250 to power the filament array.

A vacuum channels 714 are also formed on the bottom surface of the porator backing 710. This allows the applicator to uniformly apply a vacuum, through the open space between filaments of the active area of the filament array, to the porated area on the skin while porating.

Fork

In the second embodiment, preferably, the fork 910 may be attached to the casting sheet 850, as shown in FIG. 25 and FIG. 29. The fork 910 aims to hold the patch at a given position of the porator. The fork 910 comprises: two claws 912 to be fitted in the slots 722 of the porator; and a flat, recessed from the bottom, part 914 to hold the first part 812 of the adhesive sheet 810 via the first part 852 of the casting sheet 850. In FIG. 29 (*a*), the first part 852 of the casting sheet 850 and the first part 812 of the adhesive sheet 810 are set on the bottom surface of the flat part 914. The first part 852 of the casting sheet 850 is fixed to the fork.

The fork 910 is a holder for more accurately set the patch at a fixed position laterally apart from the porator. The adhesive sheet is guided between the two claws 912 thereof and more accurately adheres to the skin surface.

The fork 910 is fitted in the porator with two claws 912, but will slide off effortlessly when the user pulls away as an option, subtle bump-overs could be integrated in the fork's tips to hold the fork better during transport and handling. The fork is a clear indicator that the casting sheet needs to be removed after application.

Two slits 722 for inserting the two claws of the fork 910 are formed on the front end surface of the porator backing 710, as shown in FIG. 28.

Without the fork, the positioning (or alignment) of the patch over the porated area is inconsistent from one application to the next. During first steps of an application, while patch is still in the air, the fork provides stability and maintains the leading edge of the patch taut and parallel to the skin, while ensuring a constant distance between the patch's first contact with the skin and the filament array. Otherwise, the first part of a patch (812+852) will be at the same angle to the skin as θ1. Once the porator and patch touch the skin, the fork 910 also provides mechanical pressure to the first part 812 of the skin adhesive 810, thus assuring better adherence to the skin and providing more force to hold the patch in place while porator, after the pores are formed, slides out.

Figure 30:
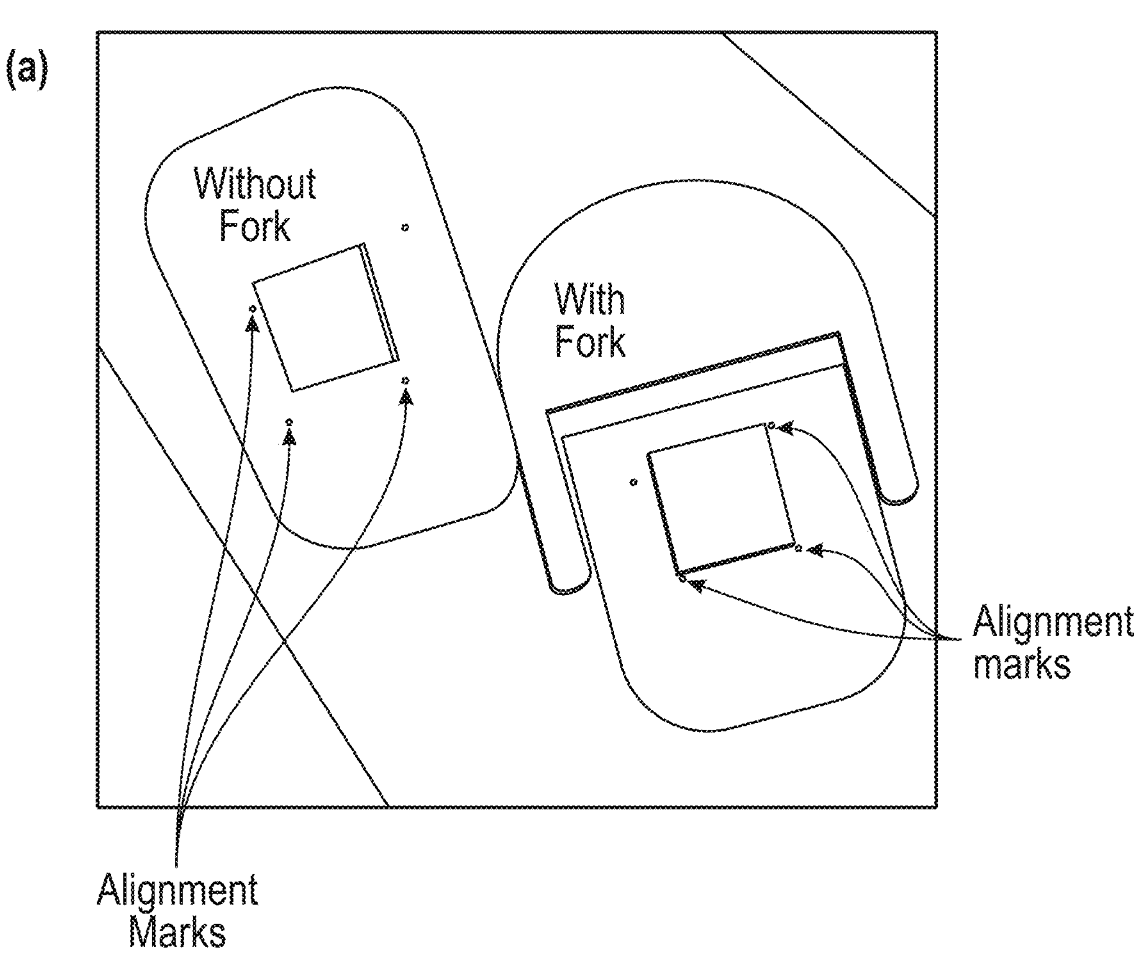
FIG. 30(*a*)-(*b*) shows the action of the fork.
Figure 30:
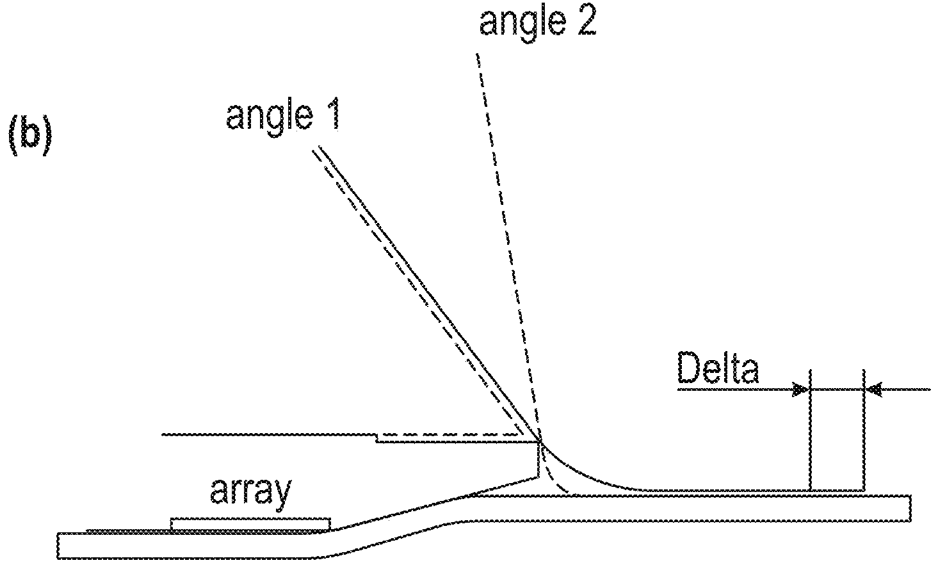

As shown in FIG. 30, (a), with fork present, the preferable positioning can be obtained. When the fork is absent, due to insufficient structural firmness of the first part of the patch (812+852), misalignment might happen in both lateral and longitudinal direction of the sliding. This problem may be partially compensated with changing the angle of the patch frame 920, to a shallower angle 1, FIG. 30 (*b*), but this influences the shape and industrial design of the applicator and may increase overall size of the device as a whole. A user can approach to the skin under different angles (angle 1 and angle 2 in FIG. 30 (*b*)) and cause inconsistency in length of the first part 812 of the skin patch adhesive 810 which is adhered to the skin, and with that cause misalignment of the drug patch 820 over porated are. Besides positioning problems, in order to achieve the same force of adhesion as with the fork 910 the first adhered part of the patch (812+852) must be larger, because the holding force is proportional to the adhered area and adherence. This makes patch larger and present extra material used.

The fork 910 can be made out of any solid material which can maintain firmness in the thicknesses which allow two claws 910 to slide into and out of the porator holes 722. Preferably it is a light material like a plastic, which can be easily shaped with all necessary features, utilizing current industrial processes. More specifically, it would be preferred that material can be compatible with non adhesive permanent bonding to the casting sheet 850 of the skin patch adhesive 810 utilizing current industrial processes.

Once the first part of the patch (812+852) is applied to the skin and poration sequence finished, the user will slide the applicator in the opposite direction of the fork 910. As explained earlier and illustrated in FIG. 24, the first part of the patch (812+852) is adhered to skin. Since the fork is permanently boded to the upper side of the first part 852 of the casting sheet 850, the fork 910 will slide out of the porator holes 722 and stay with the patch on skin, as in FIG. 30 (*a*). Intuitively this will indicate to the user that this part, fork 910, needs to be removed, and during that process the user will also remove the casting sheet 850 because of their permanent bonding in the first part 852 area.

Users may mishandle the patch by holding it by the fork. Therefore, side grips 718 are preferably provided on the porator, as shown in FIG. 28. The side grips 718 invite the user to hold the porator from the sides.

As shown in FIG. 25, the patch-fork assembly is mounted on the porator 700 by sliding the fork 910 in place and attaching the intervening release liner 830 on the liner attachment surface 724. The bottom release liner 840 is then attached around the porator to protect it along with the first part 812 of the patch adhesive 810.

Bottom Release Liner

As shown in FIG. 25, the bottom release liner 840 takes a shape of a footprint of the porator backing area which contacts skin and is extended, on its patch end, to protect exposed first part 812 of the patch skin adhesive 810. Besides providing protection for the adhesive its purpose is also to protect filaments of a filament array. Even though the filaments do not need extra protection while in packaging, that narrower part of the bottom release liner 840 intuitively signals to the user that one shall start peeling it off from that side.

As for the material, thickness, and release treatment of the bottom release liner, conventionally-known release liners can be referred to, compatible with first part 812 of the skin patch adhesive 810. Preferable examples of the material include, but are not limited to, silicone coated film (ex. PET film or PE film). The thickness of the bottom release liner is preferably, for example, about 20 μm-500 μm.

User Steps

The second embodiment of the present invention also requires fewer steps than the known techniques:

a. Clip on the porator-patch assembly to the applicator,
b. Remove the bottom release liner,
c. Apply the device (applicator-porator device) to skin and activate,
d. Slide the applicator away (the patch with the fork remains on the porated area),
e. Smooth over with finger (optional, since the fork does not smooth the patch like the roller or spatula),
f. Remove the casting sheet (with the fork).

INDUSTRIAL APPLICABILITY

As described above, the present invention affords a preferable positioning or aligning mechanism capable of appropriately placing the patch on the target area or the porated area.

This application is based on U.S. provisional patent application No. 62/291,752 (filing date: Feb. 5, 2016), the contents of which are incorporated in full herein.

What is claimed is:

1. A transdermal permeant application device comprising a patch application support;

a patch having an adhesive area, the adhesive area having a first part and a second part; and an intervening release liner provided between the patch application support and the patch, the intervening release liner covering the second part of the adhesive area of the patch, extending away from the patch and turning over in a curl configuration around and away from the patch to facilitate a smooth rolling peel of the intervening release liner, and being fixed to the patch application support, wherein the intervening release liner is configured not to contact and adhere to the skin during a porating process;

wherein the transdermal permeant application device further comprises:

a porating element, wherein the porating element is provided in or on the patch application support, and the porating element is adapted to form at least one pore in a skin surface;

wherein the transdermal permeant application device is configured so that, in a use situation in which the first part of the adhesive area of the patch adheres to the skin surface, and the porating element forms at least one pore in the skin surface, the patch application support with the porating element is slidable along the skin surface without lifting along the skin surface to peel the intervening release liner from the second part of the adhesive area of the patch, to adhere the second part to the skin surface and allow the patch to be positioned over a porated area.

2. The transdermal permeant application device according to claim 1, wherein the patch application support further comprises a spatula which extends to a position laterally away from the patch application support, such that, when in use, the patch application support slides along the skin surface, the spatula follows to slide on the patch and press the patch against the skin surface.

3. The transdermal permeant application device according to claim 1, further comprising a reusable body, wherein the patch application support, the patch, and the intervening release liner are replaceably attached to the reusable body.

4. The transdermal permeant application device according to claim 3, wherein the reusable body comprises a spatula which extends to a position laterally away from the patch application support, such that when, in use, the reusable body and the patch application support slide along the skin surface, the spatula follows to slide on the patch and press the patch against the skin surface.

5. The transdermal permeant application device according to claim 3, wherein the patch application support further comprises a spatula which extends to a position laterally away from the patch application support, such that when, in use, the patch application support slides along the skin surface, the spatula follows to slide on the patch and press the patch against the skin surface.

6. The transdermal permeant application device according to claim 3, wherein the reusable body further comprises a roller positioned laterally away from the patch application support, such that when in use, the reusable body and the patch application support slide along the skin surface, the roller follows to roll on an adhesive sheet and press the patch against the skin surface.

7. The transdermal permeant application device according to claim 1, wherein:

the patch is bent at a predetermined inner angle θ1, wherein inner angle θ1 is within the range of 0 degrees <θ1<180 degrees with the adhesive area facing outwardly, and a bending line thereof divides the adhesive area into the first part and the second part;

the first part is positioned laterally away from the patch application support, to adhere to the skin surface when the device is in use, the second part stands up at the inner angle θ1, with the adhesive area facing the patch application support; and the intervening release liner is provided between the patch application support and the patch, the intervening release liner covering the second part, and being fixed to the patch application support;

whereby, in a use situation in which the first part of the adhesive area of the patch adheres to the skin surface, the patch application support is slidable along the skin surface to peel the intervening release liner from the second part of the adhesive area of the patch to adhere the second part to the skin surface.

8. The transdermal permeant application device according to claim 7, further comprising a fork to hold the patch at a given position in relation to the patch application support;

wherein the fork comprises:

two claws to be fitted in the patch application support; and a flat part under which an upper side of the first part of the adhesive area is attached directly or via a casting sheet.

9. The transdermal permeant application device according to claim 1, wherein the porating element is selected from a group consisting of:

one or more elements capable of delivering thermal energy via direct contact to the skin to cause ablation to form the at least one pore in the skin surface;

one or more elements capable of delivering electrical energy via direct contact to the skin to cause ablation to form the at least one pore in the skin surface;

one or more electro-mechanical actuators, one or more lancets;

one or more micro-needles;

one or more sonic energy ablator;

one or more laser ablation elements;

one or more physical ablation elements; and one or more fluid jet puncturers.

10. The transdermal permeant application device according to claim 1, further comprising an applicator as a reusable body having a driving source therein, wherein:

the patch application support, the patch, and the intervening release liner are replaceably attached to the applicator; and the driving source is adapted to drive the porating element to form the at least one pore in the skin surface.

11. The transdermal permeant application device according to claim 1, further comprising an applicator as a reusable body having a power source therein, wherein:

the patch application support, the patch, and the intervening release liner are replaceably attached to the applicator; and the porating element is adapted to receive electric power from the power source to form the at least one pore in the skin surface by delivering thermal energy via direct contact to the skin to cause ablation of the skin.

12. The transdermal permeant application device according to claim 11, further comprising:

a porator backing; and a porator tab as the patch application support, wherein the porator tab is a band-shaped plate with one fixed end thereof fixed to the porator backing and a free end thereof, the porator tab comprising:

an objective-surface facing outwardly such that, when the device is in use, the objective-surface contacts the skin surface of a subject;

a back-surface on the opposite side of the objective-surface; and one or more filaments as the porating element in a porating area in the objective-surface of the porator tab, wherein the one or more filaments are configured to generate heat to form one or more micropores in the skin of the subject, and wherein:

the patch is positioned on a back-surface side of the porator tab, the patch having an adhesive sheet and a reservoir placed on an adhesive surface of the adhesive sheet;

the reservoir releasably contains a permeant to be delivered through the micropores, and is alignedly positioned on the back at a position corresponding to the porating area, with the adhesive surface of the adhesive sheet facing the subject side, and the adhesive sheet comprises:

the first part extending from the free end and both longitudinal side edges of the porator tab, is configured to adhere to the skin surface; and the second part which is a remaining part, not extending from the porator tab; and wherein the intervening release liner is provided between the porator tab and the patch is fixed to the porator tab, the intervening release liner covering the adhesive surface of the second part and the reservoir, and extending away from the patch and turning over;

whereby, in a use situation in which the first part of the adhesive sheet adheres to the skin surface, the porator tab is slidable along the skin surface to the outside of the covering area of the adhesive sheet, to peel the intervening release liner from the patch to allow the reservoir to alignedly cover the porated area, and to adhere the adhesive surface of the second part to the skin surface.

13. The transdermal permeant application device according to claim 12, wherein the porator backing further comprises a spatula which extends to a position laterally away from the porator tab, such that when, in use of the device, the porator tab slides towards its fixed end side along the skin surface, the spatula follows to slide on the adhesive sheet and press the adhesive sheet against the skin surface to smooth the adhesive sheet.

14. The transdermal permeant application device according to claim 12, wherein the applicator further comprises a spatula which extends to a position laterally away from the porator tab, such that when, in use of the device, the porator tab slides towards its fixed end side along the skin surface, the spatula follows to slide on the adhesive sheet and press the adhesive sheet against the skin surface to smooth the adhesive sheet.

15. The transdermal permeant application device according to claim 12, wherein the applicator further comprises a roller positioned laterally away from the porator tab, such that when in use of the device, the porator tab slides towards its fixed end side along the skin surface, the roller follows to roll on the adhesive sheet and press the adhesive sheet against the skin surface to smooth the adhesive sheet.

16. The transdermal permeant application device according to claim 12, wherein the applicator further comprises a vacuum source, and the porator tab comprises one or more paths to apply a vacuum sucking force from the vacuum source to the skin surface.

17. The transdermal permeant application device according to claim 11, further comprising:

a porator backing with the patch application support, wherein the patch application support comprises:

an objective-surface facing outwardly such that, when the device is in use, the objective-surface contacts a skin surface of a subject; and one or more filaments as the porating element in a porating area in the objective-surface, wherein the one or more filaments are configured to generate heat to form one or more micropores in the skin of the subject; and wherein:

the patch is detachably attached to the porator backing or the applicator, and the patch has an adhesive sheet and a reservoir placed on an adhesive surface of the adhesive sheet;

the reservoir releasably contains a permeant to be delivered through the micropores;

the adhesive sheet is bent at a predetermined inner angle $\theta 1$, wherein inner angle $\theta 1$ is within the range of 0 degrees $<\theta 1<180$ degrees with the adhesive surface facing outwardly, and a bending line thereof divides the adhesive sheet into the first part and the second part;

the first part is positioned laterally away from the porator backing, to adhere to the skin surface when the device is in use;

the bending line is located on the side closer to the porating area in an outer circumference of the first part;

the second part stands up at the inner angle $\theta 1$, with the adhesive surface facing the porating area;

the reservoir is positioned on the adhesive surface of the second part, such that the reservoir and the porating area are located symmetrically with respect to the bending line; and the intervening release liner is provided between the patch application support and patch, the intervening release liner covering the adhesive surface of the second part and the reservoir, and being fixed to the patch application support or the porator backing;

wherein the device is configured so that in a use situation in which the first part of the adhesive sheet adheres to the skin surface, the applicator and the porator backing with the patch application support are slidable along the skin surface to outside of the area to be covered with the adhesive sheet, to peel the intervening release liner from the patch to allow the reservoir to alignedly cover the porated area, and to adhere the adhesive surface of the second part to the skin surface.

18. The transdermal permeant application device according to claim 17, wherein the applicator further comprises a vacuum source, and the patch application support comprises one or more paths to apply a vacuum sucking force from the vacuum source to the skin surface.

19. The transdermal permeant application device according to claim 17, further comprising a fork to hold the patch at a given position in relation to the patch application support;

wherein the fork comprises:

two claws to be fitted in the porator backing; and a flat part under which an upper side of the first part of the adhesive sheet is attached directly or via a casting sheet.

* * * * *